United States Patent
Okuda et al.

(10) Patent No.: US 11,674,946 B2
(45) Date of Patent: Jun. 13, 2023

(54) OIL CONDITION ESTIMATION APPARATUS, VEHICLE CONTROL APPARATUS, VEHICLE CONTROL SYSTEM, AND DATA ANALYSIS APPARATUS

(71) Applicant: TOYOTA JIDOSHA KABUSHIKI KAISHA, Toyota (JP)

(72) Inventors: Koichi Okuda, Toyota (JP); Atsushi Tabata, Okazaki (JP); Kota Fujii, Nissin (JP); Ken Imamura, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 211 days.

(21) Appl. No.: 17/210,017

(22) Filed: Mar. 23, 2021

(65) Prior Publication Data

US 2021/0341457 A1 Nov. 4, 2021

(30) Foreign Application Priority Data

May 1, 2020 (JP) .............................. JP2020-081306

(51) Int. Cl.
*G01N 33/28* (2006.01)
*G07C 5/04* (2006.01)

(52) U.S. Cl.
CPC ........... *G01N 33/2888* (2013.01); *G07C 5/04* (2013.01)

(58) Field of Classification Search
CPC .............................. G01N 33/2888; G07C 5/04
See application file for complete search history.

(56) References Cited

U.S. PATENT DOCUMENTS

| | | | |
|---|---|---|---|
| 2005/0288848 A1* | 12/2005 | Ha | G01N 33/2888 701/114 |
| 2008/0218325 A1* | 9/2008 | Halalay | G01N 33/2888 324/698 |
| 2009/0299933 A1 | 12/2009 | Aoyama et al. | |
| 2009/0312927 A1* | 12/2009 | Ishiwada | F16H 61/20 701/60 |
| 2015/0274154 A1 | 10/2015 | Tsuda et al. | |
| 2016/0169859 A1 | 6/2016 | Yamashita | |

(Continued)

FOREIGN PATENT DOCUMENTS

| | | |
|---|---|---|
| DE | 11 2013 004 032 T5 | 5/2015 |
| DE | 10 2007 026 943 B4 | 1/2016 |
| JP | 2002-340160 A | 11/2002 |

(Continued)

*Primary Examiner* — Jaime Figueroa
*Assistant Examiner* — Joshua Alexander Garza
(74) *Attorney, Agent, or Firm* — Oliff PLC

(57) ABSTRACT

An oil condition estimation apparatus to be applied to a vehicle in which oil is agitated by a rotator includes a storage device and an execution device. The storage device stores mapping data for defining mapping. The mapping includes, as input variables, a speed variable indicating a rotation speed of the rotator, and a pressure variable indicating a pressure of the oil, and includes, as an output variable, an air bubble variable related to air bubbles contained in the oil. The execution device executes an acquisition process for acquiring values of the input variables, and a calculation process for calculating a value of the output variable by inputting, to the mapping, the values of the input variables acquired through the acquisition process.

14 Claims, 10 Drawing Sheets

(56) References Cited

U.S. PATENT DOCUMENTS

2018/0328906 A1* 11/2018 Yoshida .................. G01N 21/59
2020/0182853 A1*  6/2020 Fukunaga .............. F01M 11/10

FOREIGN PATENT DOCUMENTS

| JP | 2008-287626 A | 11/2008 |
| JP | 2009-288934 A | 12/2009 |
| JP | 2011-179627 A |  9/2011 |
| JP | 2016-114471 A |  6/2016 |

\* cited by examiner

OIL CONDITION ESTIMATION APPARATUS, VEHICLE CONTROL APPARATUS, VEHICLE CONTROL SYSTEM, AND DATA ANALYSIS APPARATUS

CROSS-REFERENCE TO RELATED APPLICATION

This application claims priority to Japanese Patent Application No. 2020-081306 filed on May 1, 2020, incorporated herein by reference in its entirety.

BACKGROUND

1. Technical Field

The present disclosure relates to an oil condition estimation apparatus, a vehicle control apparatus, a vehicle control system, and a data analysis apparatus.

2. Description of Related Art

For example, Japanese Unexamined Patent Application Publication No. 2011-179627 (JP 2011-179627 A) describes an apparatus configured such that update amounts of an air inclusion amount in lubricating oil are sequentially calculated based on rotation speeds of a rotational shaft of an on-board rotating machine coupled to a power split device, and the air inclusion amount is calculated based on the calculated update amounts.

SUMMARY

Air inclusion is not determined based only on the rotation speed of the rotating machine. Therefore, the air inclusion amount cannot always be calculated with high accuracy based only on the rotation speed of the rotating machine.

The present disclosure relates to an oil condition estimation apparatus, a vehicle control apparatus, a vehicle control system, and a data analysis apparatus in which the value of an air bubble variable can be calculated with high accuracy without being calculated based only on a rotation speed of a rotational shaft of a rotating machine mounted on a vehicle. An oil condition estimation apparatus to be applied to a vehicle in which oil is agitated by a rotator according to a first aspect of the present disclosure includes a storage device and an execution device. The storage device is configured to store mapping data for defining mapping. The mapping includes, as input variables, a speed variable indicating a rotation speed of the rotator, and a pressure variable indicating a pressure of the oil, and includes, as an output variable, an air bubble variable related to air bubbles contained in the oil. The execution device is configured to execute an acquisition process for acquiring values of the input variables, and a calculation process for calculating a value of the output variable by inputting, to the mapping, the values of the input variables that are acquired through the acquisition process.

The amount of air bubbles contained in the oil depends on the pressure of the oil. The oil condition estimation apparatus of the first aspect calculates the value of the air bubble variable related to the air bubbles contained in the oil based not only on the rotation speed of the rotator that agitates the oil, but also on the pressure of the oil. Therefore, the value of the air bubble variable can be calculated with higher accuracy as compared to a case where the value of the air bubble variable is calculated based only on the rotation speed of the rotator.

In the oil condition estimation apparatus of the first aspect, the input variables may include a temperature variable indicating a temperature of the oil. The amount of air bubbles contained in the oil may vary depending on the temperature of the oil even at the same rotation speed of the rotator and at the same pressure of the oil. Since the oil condition estimation apparatus having the configuration described above calculates the value of the air bubble variable based on the temperature variable, the value of the air bubble variable can be calculated with higher accuracy as compared to a case where reference is not made to the temperature variable.

In the oil condition estimation apparatus of the first aspect, the oil may be used to hydraulically drive a transmission to change a gear ratio of the transmission. The transmission is configured to change the gear ratio, which is a ratio between a rotation speed of a rotational shaft of an on-board prime mover and a rotation speed of a driving wheel. The speed variable may include a vehicle speed. The pressure variable may include an accelerator operation amount.

The oil for hydraulically driving the transmission is agitated by the rotator in the transmission. The rotation speed of the rotator is proportional to the vehicle speed. The amount of air bubbles generated when the rotator agitates the oil depends on the pressure of the oil. The pressure of the oil when a driving force of the vehicle is large tends to be higher than the pressure of the oil when the driving force is small. In other words, the pressure of the oil when the accelerator operation amount is large tends to be higher than the pressure of the oil when the accelerator operation amount is small. Since the oil condition estimation apparatus having the configuration described above uses the vehicle speed and the accelerator operation amount, the value of the air bubble variable can be calculated by grasping the rotation speed of the rotator that agitates the oil and the pressure of the oil with high accuracy.

In the oil condition estimation apparatus of the first aspect, the input variables may include at least one of a stop time variable indicating a time during which the rotator is stopped, and a rotation time variable indicating a time during which the rotator is rotating.

Although the amount of air bubbles in the oil increases when the oil is agitated, the amount of air bubbles gradually decreases through continuation of a state in which the oil is not agitated. Since the oil condition estimation apparatus of the first aspect calculates the value of the air bubble variable based on at least one of the stop time variable and the rotation time variable, the value of the air bubble variable can reflect the increase in the amount of air bubbles in the state in which the oil is agitated or the decrease in the amount of air bubbles in the state in which the oil is not agitated.

In the oil condition estimation apparatus of the first aspect, the input variables of the mapping may include time-series data of the speed variable and time-series data of the pressure variable. The acquisition process may include a process of acquiring the time-series data of the speed variable and the time-series data of the pressure variable. The calculation process may be a process of calculating the value of the output variable by inputting, to the mapping, the time-series data of the speed variable and the time-series data of the pressure variable that are acquired through the acquisition process.

When the oil is agitated, the amount of air bubbles in the oil increases. The rate of the increase when the rotation speed of the rotator that agitates the oil is high is greater than the rate of the increase when the rotation speed is low. The rate of the increase in the amount of air bubbles in the oil through the agitation when the pressure of the oil is high is greater than the rate of the increase when the pressure of the oil is low. Although the amount of air bubbles in the oil increases when the oil is agitated, the amount of air bubbles gradually decreases through continuation of a state in which the oil is not agitated. The oil condition estimation apparatus having the configuration described above can acquire, based on the time-series data, information about how the oil is agitated and information about a period during which the oil is not agitated. Thus, the value of the air bubble variable can be calculated more accurately.

In the oil condition estimation apparatus of the first aspect, the air bubble variable may include an update amount of an air bubble amount in the oil. The mapping may include a function approximator configured to output the update amount of the air bubble amount by inputting the values of the input variables. The calculation process may include a process of repeatedly calculating the value of the output variable by inputting, to the mapping, the values of the input variables that are repeatedly acquired through the acquisition process, and updating the air bubble amount based on the value of the output variable that is calculated each time.

A change amount of air bubbles in the oil in a predetermined period can be grasped based on the rotation speed of the rotator and the pressure of the oil in the predetermined period. The oil condition estimation apparatus having the configuration described above calculates the change amount of the air bubble amount in the oil in the predetermined period by inputting, for example, the value of the rotation variable and the value of the pressure variable to the mapping. The air bubble amount in the oil can be calculated by updating the air bubble amount in the oil with the change amount used as the update amount.

In the oil condition estimation apparatus of the first aspect, the air bubble variable may include an air bubble amount in the oil. The mapping may include a recurrent neural network configured to output the air bubble amount by inputting the values of the input variables.

A change amount of air bubbles in the oil in a predetermined period can be grasped based on the rotation speed of the rotator and the pressure of the oil in the predetermined period. With the recurrent neural network, the value of the output variable can be calculated based not only on values of the input variables acquired once, but also on values of the input variables in the past. In the oil condition estimation apparatus having the configuration described above, the value of the air bubble variable can be calculated by using the recurrent neural network based on records of the value of the speed variable and the value of the pressure variable in the past. In the configuration described above, records in the distant past are sufficiently reflected in the value of the output variable in the recurrent neural network. Thus, the air bubble variable can be the air bubble amount itself instead of the change amount of the air bubble amount in the predetermined period set in advance.

In the oil condition estimation apparatus of the first aspect, the air bubble variable may include a necessary stop time of the rotator that is necessary to reduce an air bubble amount in the oil to a specified amount or smaller.

Although the amount of air bubbles in the oil increases when the oil is agitated, the amount of air bubbles gradually decreases through continuation of a state in which the oil is not agitated. The stop time of the rotator that is necessary to reduce the air bubble amount in the oil to the specified amount or smaller depends on a current air bubble amount in the oil. Therefore, the necessary stop time depends on the value of the speed variable and the value of the pressure variable. In the oil condition estimation apparatus having the configuration described above, the necessary stop time can be calculated based on the values of those variables.

In the oil condition estimation apparatus of the first aspect, the output variable may include a determination variable indicating whether replacement of the oil is necessary. The oil contains an anti-foaming agent or the like. The anti-foaming agent or the like is sheared through the rotation of the rotator. Therefore, the amount of air bubbles in the oil is likely to increase when deterioration of the anti-foaming agent or the like advances. In this case, it is desirable to replace the oil.

Even if any trouble occurs due to an excessive increase in the amount of air bubbles, the amount of air bubbles gradually decreases through continuation of a state in which the oil is not agitated. Even if the vehicle is brought to a repair shop or the like because of a problem in the oil, air bubbles are not excessively present in the oil in a case where the oil is not agitated for a long period.

The oil condition estimation apparatus having the configuration described above grasps records of the shear of components such as the anti-foaming agent in the oil based on the speed variable and the like, and calculates, based on the records, a value of the determination variable indicating whether the replacement of the oil is necessary. Thus, it is possible to determine whether the replacement of the oil is necessary irrespective of whether the air bubble amount in the oil is large or small when the oil is checked.

A vehicle control apparatus according to a second aspect of the present disclosure includes the oil condition estimation apparatus of the first aspect. The oil is hydraulic oil whose pressure is adjusted by a hydraulic control device. The air bubble variable includes at least one of an air bubble amount in the oil and an update amount of the air bubble amount in the oil. The execution device is configured to execute, when the air bubble amount calculated through the calculation process is equal to or larger than a threshold, an addressing process for reducing the pressure by operating the hydraulic control device.

The amount of air bubbles generated through the agitation of the oil by the rotator when the pressure of the oil is high is larger than the amount of air bubbles when the pressure of the oil is low. Since the oil condition estimation apparatus of the second aspect reduces the pressure when the air bubble amount increases, a further increase in the air bubble amount can be suppressed.

A vehicle control apparatus according to a third aspect of the present disclosure includes the oil condition estimation apparatus of the first aspect. The oil hydraulically drives a transmission to change a gear ratio of the transmission, the gear ratio being a ratio between a rotation speed of a rotational shaft of an on-board prime mover and a rotation speed of a driving wheel. The air bubble variable includes at least one of an air bubble amount in the oil and an update amount of the air bubble amount in the oil. The execution device is configured to execute, when the air bubble amount calculated through the calculation process is equal to or larger than a threshold, an addressing process for limiting a torque of the on-board prime mover to a smaller value.

The amount of air bubbles generated through the agitation of the oil by the rotator when the pressure of the oil is high is larger than the amount of air bubbles when the pressure of the oil is low. The pressure of the oil for hydraulically driving the transmission when the torque of the on-board prime mover is large tends to be higher than the pressure of the oil when the torque is small. Since the oil condition estimation apparatus of the third aspect limits the torque of the on-board prime mover to a smaller value when the air bubble amount is large, the pressure of the oil can be limited to a smaller value. Furthermore, a further increase in the air bubble amount can be suppressed.

A vehicle control apparatus according to a fourth aspect of the present disclosure includes the oil condition estimation apparatus of the first aspect. The execution device is configured to execute, when a value of the determination variable calculated through the calculation process is a value indicating that the replacement of the oil is necessary, an addressing process for notifying, by operating a notification device, a user that the replacement of the oil is necessary.

In the vehicle control apparatus of the fourth aspect, when the replacement of the oil is necessary, the user is notified of this information. Thus, the user can be informed about what to do.

A vehicle control system according to a fifth aspect of the present disclosure includes the vehicle control apparatus. The execution device includes a first execution device that is provided in the vehicle and a second execution device that is not provided in the vehicle. The second execution device is configured to execute at least the calculation process to the first execution device, and a transmission process for transmitting a calculation result obtained through the calculation process. The first execution device is configured to execute at least a vehicle-side reception process for receiving the calculation result obtained through the calculation process from the second execution device and the addressing process.

In the vehicle control system of the fifth aspect, the second execution device executes the calculation process. Thus, a calculation load on the first execution device can be reduced as compared to a case where the first execution device executes the calculation process.

A vehicle control apparatus to be applied to a vehicle in which oil is agitated by a rotator according to a sixth aspect of the present disclosure includes a storage device and an execution device. The storage device is provided in the vehicle and configured to store mapping data for defining mapping. The mapping includes, as input variables, a speed variable indicating a rotation speed of the rotator, and a pressure variable indicating a pressure of the oil, and includes, as an output variable, an air bubble variable related to air bubbles contained in the oil. The execution device is provided in the vehicle and configured to execute at least a vehicle-side reception process for receiving a calculation result obtained through a calculation process executed by a device not provided in the vehicle and an addressing process for addressing the calculation result. The calculation process is a process that calculates a value of the output variable by inputting the values of the input variables to the mapping. The addressing process is at least one of: (i) a process that reduces the pressure of the oil by operating the hydraulic control device provided in the vehicle, when the air bubble amount calculated through the calculation process is equal to or larger than a threshold; (ii) the addressing process is a process that limits a torque of the on-board prime mover to a smaller value, when the air bubble amount calculated through the calculation process is equal to or larger than a threshold, and (iii) the addressing process is a process that notifies a user that the replacement of the oil is necessary, when a value of the determination variable calculated through the calculation process is a value indicating that the replacement of the oil is necessary.

A data analysis apparatus to be applied to a vehicle in which oil is agitated by a rotator according to according to a seventh aspect of the present disclosure includes a storage device and an execution device. The storage device is not provided in the vehicle and configured to store mapping data for defining mapping. The mapping includes, as input variables, a speed variable indicating a rotation speed of the rotator, and a pressure variable indicating a pressure of the oil, and includes, as an output variable, an air bubble variable related to air bubbles contained in the oil. The execution device is not provided in the vehicle and configured to execute at least the calculation process and a transmission process. The calculation process is a process that calculates a value of the output variable by inputting the values of the input variables to the mapping. The transmission process is a process that transmits a calculation result obtained through the calculation process to a device provided in the vehicle.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Figure 1:
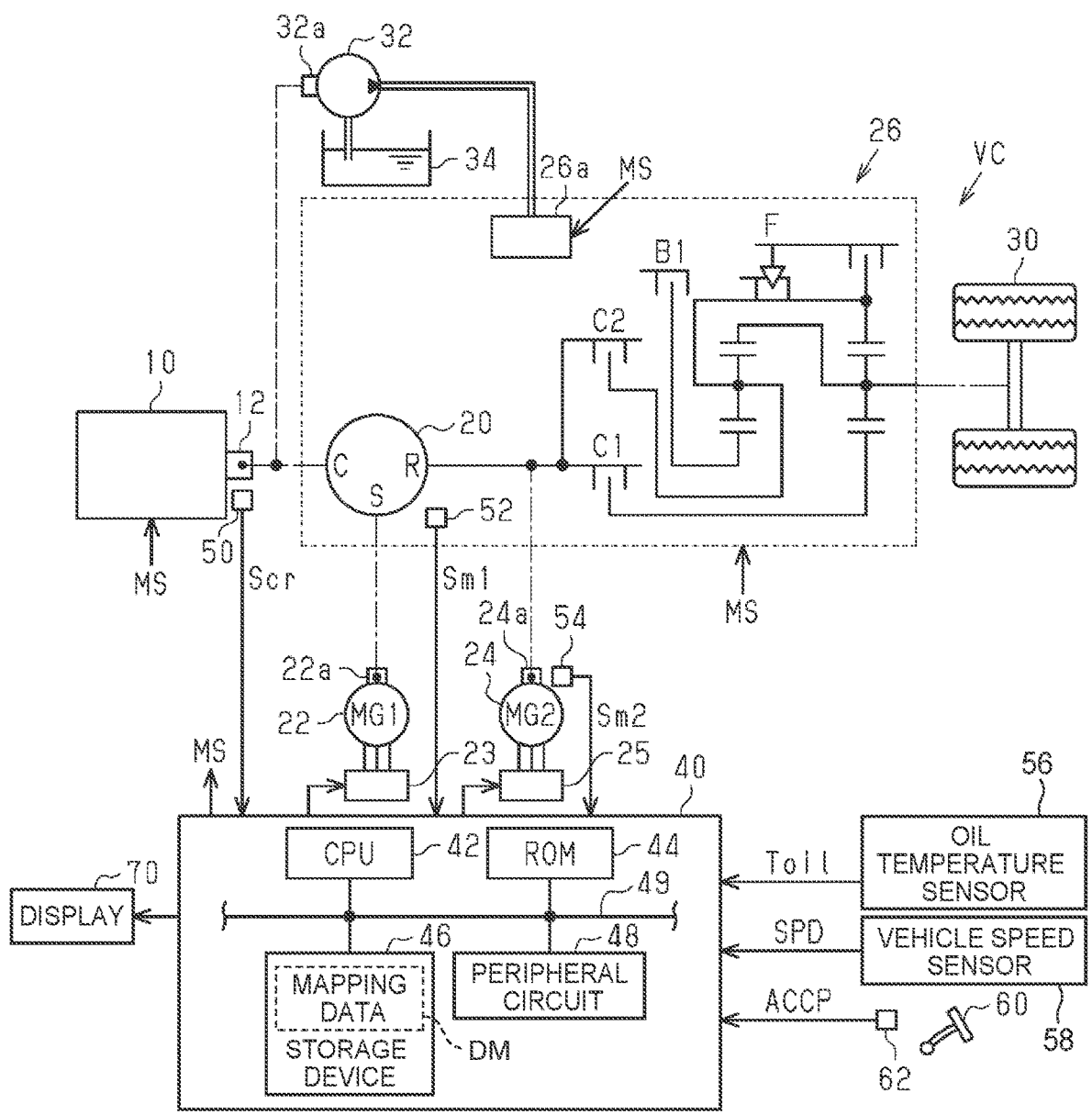
FIG. 1 is a diagram illustrating a control apparatus and a power transmission apparatus according to a first embodiment of the present disclosure.

A first embodiment is described below with reference to the drawings. As illustrated in FIG. 1, a power split device 20 is mechanically coupled to a crankshaft 12 that is a rotational shaft of an internal combustion engine 10 serving as an on-board prime mover. The power split device 20 splits power of the internal combustion engine 10, a first motor generator 22, and a second motor generator 24. The power split device 20 includes a planetary gearing mechanism. The crankshaft 12 is mechanically coupled to a carrier C of the planetary gearing mechanism. A rotational shaft 22a of the first motor generator 22 is mechanically coupled to a sun gear S of the planetary gearing mechanism. A rotational shaft 24a of the second motor generator 24 is mechanically coupled to a ring gear R of the planetary gearing mechanism. An output voltage of a first inverter 23 is applied to a terminal of the first motor generator 22. An output voltage of a second inverter 25 is applied to a terminal of the second motor generator 24.

Driving wheels 30 are mechanically coupled to the ring gear R of the power split device 20 via a transmission 26 in addition to the rotational shaft 24a of the second motor generator 24. A driven shaft 32a of an oil pump 32 is mechanically coupled to the carrier C. The oil pump 32 circulates oil in an oil pan 34 through the power split device 20 as lubricating oil, and ejects the oil to the transmission 26 as hydraulic oil. A hydraulic control circuit 26a in the transmission 26 adjusts a pressure of the hydraulic oil ejected from the oil pump 32 to use the hydraulic oil.

A control apparatus 40 controls the internal combustion engine 10, and operates various operation portions of the internal combustion engine 10 to control, for example, a torque and an exhaust gas component ratio that are control amounts. The control apparatus 40 controls the first motor generator 22, and operates the first inverter 23 to control, for example, a torque and a rotation speed that are control amounts. The control apparatus 40 controls the second motor generator 24, and operates the second inverter 25 to control, for example, a torque and a rotation speed that are control amounts.

To control the control amounts, the control apparatus 40 refers to an output signal Scr from a crank angle sensor 50, an output signal Sm1 from a first rotation angle sensor 52, and an output signal Sm2 from a second rotation angle sensor 54. The first rotation angle sensor 52 detects a rotation angle of the rotational shaft 22a of the first motor generator 22. The second rotation angle sensor 54 detects a rotation angle of the rotational shaft 24a of the second motor generator 24. The control apparatus 40 also refers to an oil temperature Toil that is a temperature of the oil detected by an oil temperature sensor 56, a vehicle speed SPD detected by a vehicle speed sensor 58, and an accelerator operation amount ACCP that is an operation amount of an accelerator pedal 60 detected by an accelerator sensor 62.

The control apparatus 40 includes a central processing unit (CPU) 42, a read-only memory (ROM) 44, a storage device 46 that is an electrically rewritable non-volatile memory, and a peripheral circuit 48, which are communicable with each other via a local network 49. The peripheral circuit 48 includes a circuit configured to generate a clock signal for defining internal operations, a power supply circuit, and a reset circuit. The control apparatus 40 controls the control amounts such that the CPU 42 executes programs stored in the ROM 44.

Figure 2:
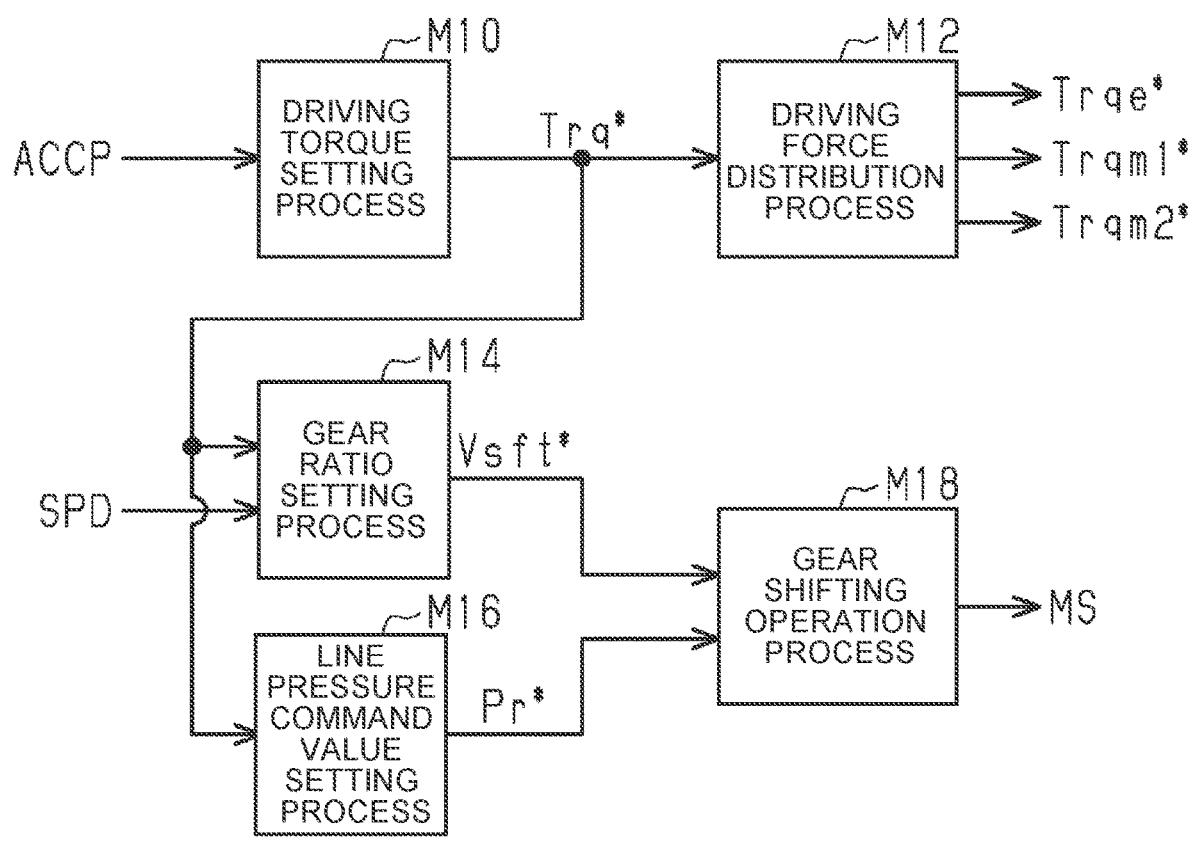
FIG. 2 is a block diagram illustrating processes to be executed by the control apparatus according to the first embodiment.

FIG. 2 illustrates a part of processes to be executed by the control apparatus 40. The processes illustrated in FIG. 2 are implemented such that the CPU 42 repeatedly executes the programs stored in the ROM 44 in, for example, every predetermined period.

In a driving torque setting process M10, the accelerator operation amount ACCP is input. When the accelerator operation amount ACCP is large, a driving torque command value Trq* is calculated as a larger value than the value when the accelerator operation amount ACCP is small. The driving torque command value Trq* is a command value of a torque to be applied to the driving wheels 30.

In a driving force distribution process M12, a torque command value Trqe* for the internal combustion engine 10, a torque command value Trqm1* for the first motor generator 22, and a torque command value Trqm2* for the second motor generator 24 are set based on the driving torque command value Trq*. The torque command values Trqe*, Trqm1*, and Trqm2* are values at which the torque to be generated by the internal combustion engine 10, the first motor generator 22, and the second motor generator 24 and applied to the driving wheels 30 is the driving torque command value Trq*.

In a gear ratio setting process M14, a gear ratio command value Vsft* is set based on the vehicle speed SPD and the driving torque command value Trq*. The gear ratio command value Vsft* is a command value of a gear ratio of the transmission 26. In a line pressure command value setting process M16, a line pressure command value Pr* is set based on the driving torque command value Trq*. The line pressure command value Pr* is a command value of the pressure of the oil in the transmission 26. Specifically, when the driving torque command value Trq* is large, the line pressure command value Pr* is set to a larger value than the value when the driving torque command value Trq* is small.

In a gear shifting operation process M18, an operation signal MS is output to the transmission 26 to control the pressure of the oil at the line pressure command value Pr* or control the gear ratio at the gear ratio command value Vsft*. The oil is used to hydraulically drive friction engagement elements such as clutches and brakes in the transmission 26 based on the line pressure command value Pr*.

Figure 3:
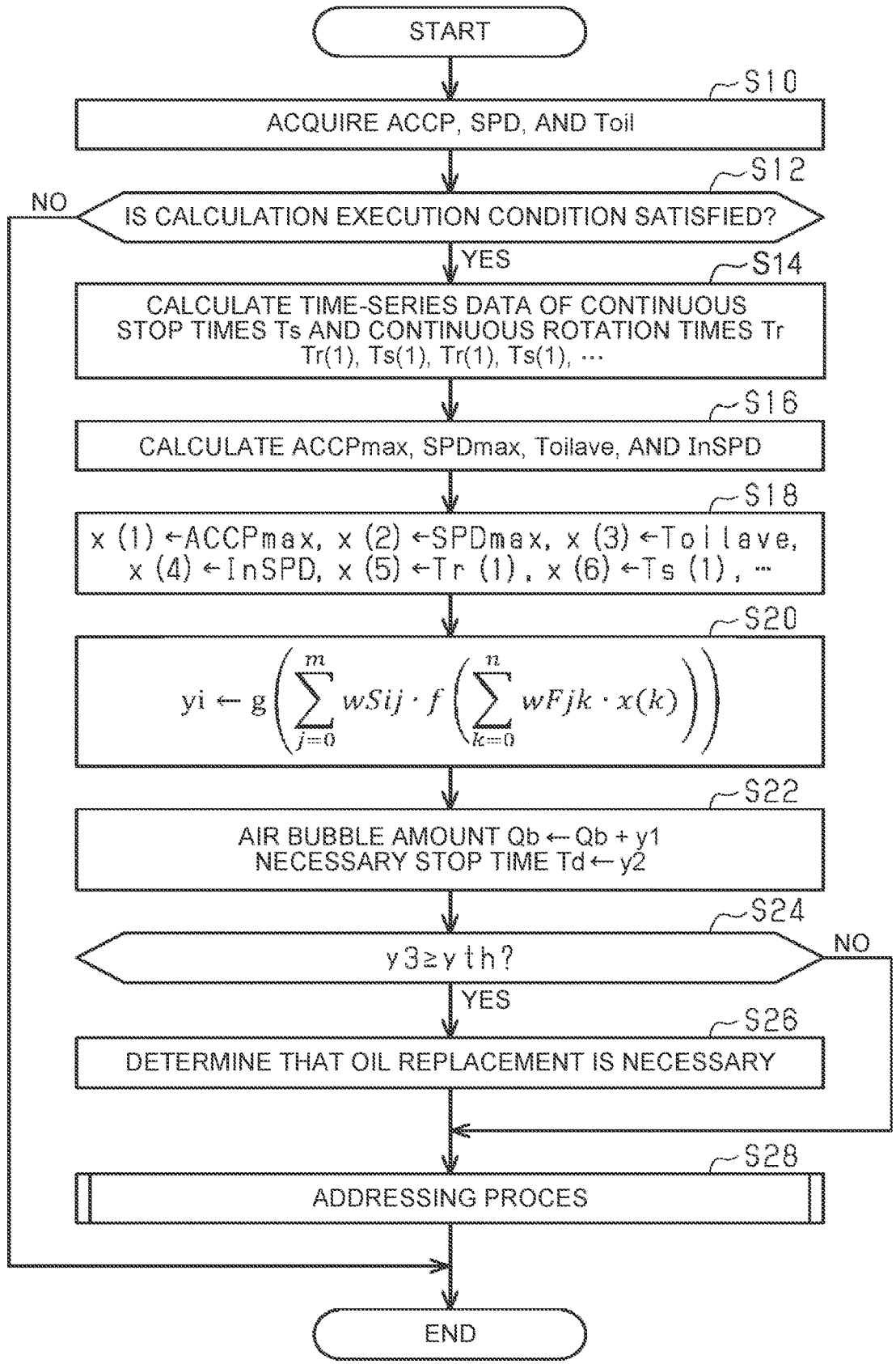
FIG. 3 is a flowchart illustrating a procedure of a process to be executed by the control apparatus according to the first embodiment.

The control apparatus 40 grasps an air bubble amount in the oil, and executes an addressing process when a problem arises. This process is described below. FIG. 3 illustrates a procedure of the process to be executed by the control apparatus 40 according to this embodiment. The process illustrated in FIG. 3 is implemented such that the CPU 42 repeatedly executes a program stored in the ROM 44 in, for example, every predetermined period. Step numbers of each process are hereinafter represented by numerals prefixed with "S".

In a series of processes illustrated in FIG. 3, the CPU 42 first acquires the accelerator operation amount ACCP, the vehicle speed SPD, and the oil temperature Toil (S10). Next, the CPU 42 determines whether a calculation execution condition related to the air bubble amount in the oil is satisfied (S12). In this embodiment, the CPU 42 determines that the calculation execution condition is satisfied when a predetermined period set in advance elapses from a timing of execution of a previous calculation process.

When the CPU 42 determines that the calculation execution condition is satisfied (S12: YES), the CPU 42 acquires values of input variables for use in the calculation process through processes of S14 and S16. That is, the CPU 42 acquires time-series data of continuous stop times Ts and continuous rotation times Tr (S14). The continuous stop time Ts is a time during which all the three rotating machines that are the internal combustion engine 10, the first motor generator 22, and the second motor generator 24 continue to stop. The continuous rotation time Tr is a time during which at least one of the rotating machines is rotating continuously. For example, the following result is obtained when the determination result in the process of S12 is positive at a timing when at least one of the three rotating machines continues to operate for a predetermined time T1 after the timing of execution of the previous calculation process, and then all the three rotating machines continue to stop for a predetermined time T2. That is, the CPU 42 substitutes the predetermined time T1 into a continuous rotation time Tr(1), the predetermined time T2 into a continuous stop time Ts(1), and "0" into continuous rotation times Tr(2), Tr(3), - - - and continuous stop times Ts(2), Ts(3), - - - . Further, the following result is obtained when the determination result in the process of S12 is positive in a state in which, after the timing of execution of the previous calculation process, at least one of the three rotating machines operates, all the rotating machines stop, at least one of the rotating machines operates, and all the rotating machines stop. That is, the CPU 42 substitutes values larger than "0" into the continuous rotation times Tr(1) and Tr(2) and the continuous stop times Ts(1) and Ts(2), and "0" into the continuous rotation times Tr(3), Tr(4), - - - and the continuous stop times Ts(3), Ts(4), - - - .

Figure 4:
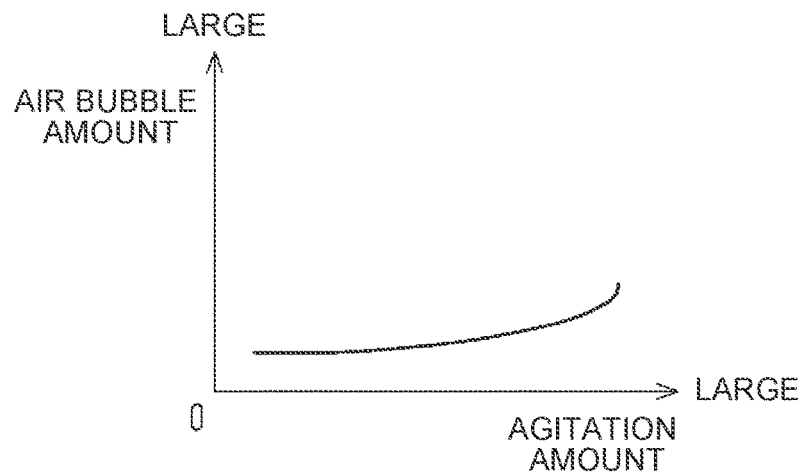
FIG. 4 is a diagram illustrating a relationship between an agitation amount and an air bubble amount according to the first embodiment.

The continuous rotation times Tr(1), Tr(2), - - - are parameters having positive correlations with the amount of air bubbles in the oil. The continuous stop times Ts(1), Ts(2), - - - are parameters having negative correlations with the amount of air bubbles in the oil. That is, air bubbles are generated when the oil is agitated by a rotator of the power split device 20 or the transmission 26. As illustrated in FIG. 4, the air bubble amount increases as the oil agitation amount increases. In FIG. 4, the "agitation amount" is larger when the rotation speed of the rotator that agitates the oil is high than the agitation amount when the rotation speed is low. At the same rotation speed, the agitation amount is larger when the agitation time is long than the agitation amount when the agitation time is short.

Figure 5:
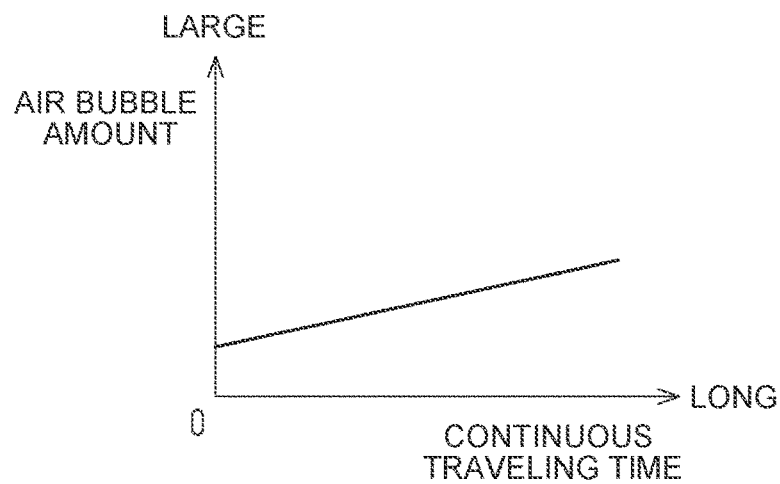
FIG. 5 is a diagram illustrating a relationship between a continuous traveling time and the air bubble amount according to the first embodiment.

FIG. 5 illustrates a relationship between the air bubble amount and a continuous traveling time during which the vehicle is traveling continuously. When the vehicle is traveling, the rotator of the power split device 20 or the transmission 26 is rotating. Therefore, this period of time may be regarded as a time during which the rotator of the power split device 20 or the transmission 26 continues to rotate, that is, the continuous rotation time Tr.

Figure 6:
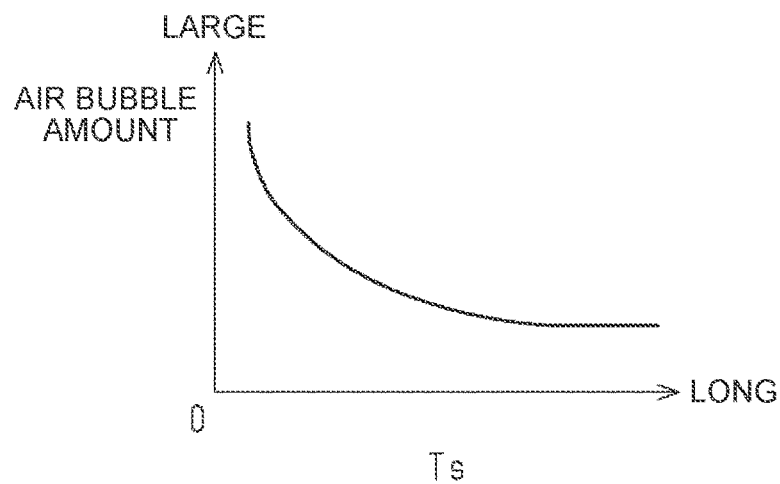
FIG. 6 is a diagram illustrating a relationship between a continuous stop time and the air bubble amount according to the first embodiment.

FIG. 6 illustrates a relationship between the continuous stop time Ts and the air bubble amount. As illustrated in FIG. 6, the air bubble amount gradually decreases as the continuous stop time Ts increases. The CPU 42 calculates a maximum value ACCPmax of the accelerator operation amount ACCP, a maximum value SPDmax of the vehicle speed SPD, an average Toilave of the oil temperature Toil, and a cumulative vehicle speed quantitative value InSPD in the predetermined period from the timing of execution of the previous calculation process to the positive determination in the current process of S12 (S16).

The accelerator operation amount ACCP is a parameter having a positive correlation with the air bubble amount. That is, the driving torque command value Trq* is set to a larger value and furthermore the line pressure command value Pr* is set to a larger value as the accelerator operation amount ACCP increases. When the line pressure command value Pr* is high, it is more likely that air bubbles are generated than when the line pressure command value Pr* is low.

Figure 7:
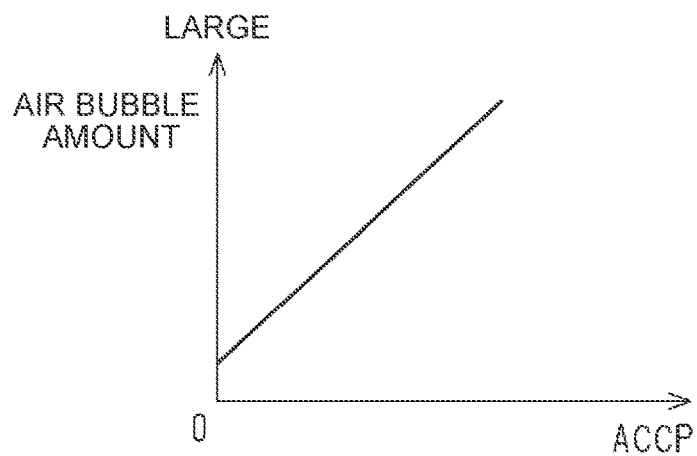
FIG. 7 is a diagram illustrating a relationship between an accelerator operation amount and the air bubble amount according to the first embodiment.

FIG. 7 illustrates a relationship between the accelerator operation amount ACCP and the air bubble amount. As illustrated in FIG. 7, the air bubble amount increases as the accelerator operation amount ACCP increases. In actuality, the air bubble amount tends to increase nonlinearly when the line pressure increases to some extent. This tendency is omitted in FIG. 7.

This embodiment particularly focuses on the fact that the air bubble amount increases as the accelerator operation amount ACCP increases. The maximum value ACCPmax of the accelerator operation amount ACCP is employed as an input variable to reduce the number of dimensions of the input variables for use in calculation of output variables described later.

The vehicle speed SPD is a parameter having a positive correlation with the air bubble amount. That is, the rotation speed of the rotator of the power split device 20 or the transmission 26 generally increases as the vehicle speed SPD increases. Therefore, the oil agitation amount increases. Thus, the air bubble amount in the oil increases as the vehicle speed SPD increases.

Figure 8:
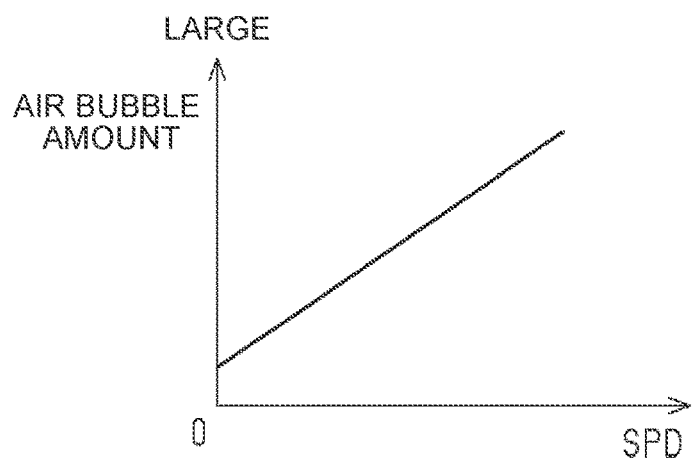
FIG. 8 is a diagram illustrating a relationship between a vehicle speed and the air bubble amount according to the first embodiment.

FIG. 8 illustrates a relationship between the vehicle speed SPD and the air bubble amount. In actuality, the air bubble amount tends to increase nonlinearly when the rotation speed of the rotator increases to some extent. This tendency is omitted in FIG. 8.

This embodiment particularly focuses on the fact that the air bubble amount increases as the vehicle speed SPD increases. The maximum value SPDmax of the vehicle speed SPD is employed as an input variable to reduce the number of dimensions of the input variables for use in the calculation of the output variables.

Figure 9:
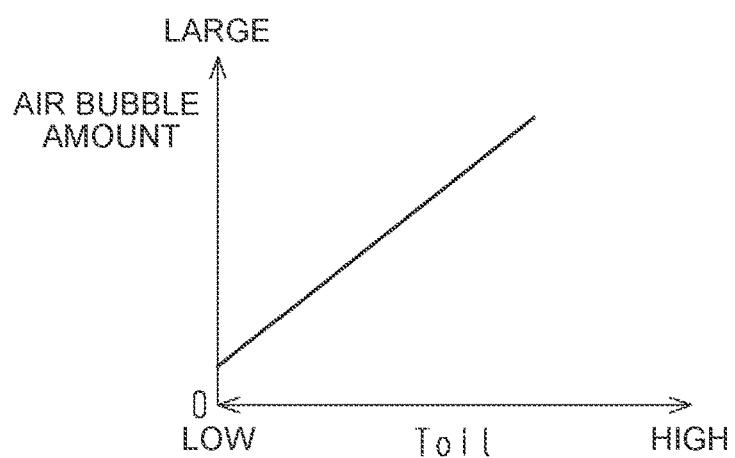
FIG. 9 is a diagram illustrating a relationship between an oil temperature and the air bubble amount according to the first embodiment.

The oil temperature Toil is a parameter having a positive correlation with the air bubble amount. FIG. 9 illustrates a relationship between the oil temperature Toil and the air bubble amount. In this embodiment, the average Toilave of the oil temperature Toil is used to reduce the number of dimensions of the input variables for use in the calculation of the output variables.

In the process of S16, the cumulative vehicle speed quantitative value InSPD is also calculated. The cumulative vehicle speed quantitative value InSPD is a weighted cumulative value of vehicle speeds SPD obtained such that the level of the vehicle speed SPD is divided into a plurality of categories and a vehicle speed SPD in a higher-level category is multiplied by a larger weighting factor. The cumulative vehicle speed quantitative value InSPD is a quantification of vehicle speeds SPD in a period to a current time from a later timing out of a timing of shipping of a vehicle VC and a timing of oil replacement.

The cumulative vehicle speed quantitative value InSPD is a variable for grasping, for example, deterioration of the oil. That is, the oil generally contains an anti-foaming agent or the like. The anti-foaming agent or the like deteriorates by being sheared through the rotation of the rotator. It is likely that air bubbles are generated when the deterioration advances. Oil replacement is necessary to exert the original function of the oil. Even if any trouble occurs in, for example, the gear shifting operation of the transmission 26 due to an abrupt increase in the amount of air bubbles in the oil that deteriorates through the rotation of the rotator, it is difficult to determine whether the oil deteriorates based on an air bubble amount during the stop of the rotator because the air bubble amount decreases through continuation of the stop of the rotator. Since the variables described above are parameters for grasping a current air bubble amount in the oil, it is difficult to grasp whether oil replacement is necessary. Therefore, the cumulative vehicle speed quantitative value InSPD is employed as a variable for determining whether oil replacement is necessary.

The cumulative vehicle speed quantitative value InSPD is not merely the sum of vehicle speeds SPD because nonlinearity is present between oil deterioration and the rotation speed of the rotator in the power transmission apparatus, and the oil deterioration is likely to be particularly conspicuous when the rotation speed of the rotator is high.

When the CPU 42 acquires the values of the variables described above, the CPU 42 substitutes the values of the variables calculated in the processes of S14 and S16 into input variables of mapping defined by mapping data DM stored in the storage device 46 illustrated in FIG. 1 (S18). That is, the CPU 42 substitutes the maximum value ACCPmax into an input variable x(1), the maximum value SPDmax into an input variable x(2), the average Toilave into an input variable x(3), the cumulative vehicle speed quantitative value InSPD into an input variable x(4), and the values of the variables calculated in the process of S14 into input variables x(5), x(6), . . . .

Next, the CPU 42 calculates output variables y1 to y3 related to air bubbles in the oil by substituting the input variables x(1), x(2), x(3), . . . into the mapping (S20).

In this embodiment, a function approximator is exemplified as the mapping. Specifically, a fully connected feedforward neural network having one intermediate layer and three nodes in an output layer is exemplified. More specifically, values of nodes in the intermediate layer are determined such that a bias parameter x(0) and the input variables x(1) to x(m) substituted by values through the process of S18 are converted by linear mapping defined by a coefficient wFjk (j=1 to m, k=0 to n), and "m" values obtained through the conversion are substituted into an activation function f. Further, the output variables y1 to y3 are determined such that the values of the nodes in the intermediate layer are converted by linear mapping defined by a coefficient wSij (i=1 to 3), and three values obtained through the conversion are substituted into an activation function g. In this embodiment, hyperbolic tangents are exemplified as the activation functions f and g.

The output variable y1 indicates an update amount of the air bubble amount in the oil. The output variable y2 indicates an estimated time required for the air bubble amount in the oil to decrease to a specified amount. The specified amount is set to an air bubble amount that causes no problem even when the vehicle travels a predetermined distance. When the value of the output variable y2 is equal to or smaller than "0", the air bubble amount in the oil is equal to or smaller than the specified amount.

The output variable y3 is a determination variable indicating whether oil replacement is necessary. In this embodiment, when the value of the output variable y3 is large, the necessity of oil replacement is higher than the necessity when the value of the output variable y3 is small.

The mapping data DM is a model trained before installed in a vehicle VC(1) by using a vehicle having the same specifications as those of the vehicle VC(1) or a power transmission apparatus including the internal combustion engine 10, the first motor generator 22, the second motor generator 24, the power split device 20, the transmission 26, and the oil pump 32. That is, input variables obtained by variously setting the condition of the power transmission apparatus are acquired, and an image of the oil in the oil pan 34 at that time is captured by an imaging apparatus. The air bubble amount in the oil is calculated by analyzing the image data. Then, the power transmission apparatus is stopped, the image data is monitored to monitor a decrease in the air bubble amount in the oil, and a time required for the air bubble amount to decrease to the specified amount is measured. When an abnormal phenomenon is detected, such as an abrupt increase in the amount of air bubbles along with the operation of the power transmission apparatus, determination is made that oil replacement is necessary. Training data is generated in this manner, and the mapping data DM is trained based on the training data. When differences between values output from the mapping data DM and values of the training data that are related to the values of the output variables y1 to y3 are equal to or smaller than predetermined values, determination is made that the training is completed, and the mapping data DM is stored in the storage device 46.

The CPU 42 updates an air bubble amount Qb by adding the value of the output variable y1 to the air bubble amount Qb, and substitutes the value of the output variable y2 into a necessary stop time Td, which is an estimated time required for the air bubble amount in the oil to decrease to the specified amount (S22).

Next, the CPU 42 determines whether the value of the output variable y3 is equal to or larger than a threshold yth (S24). This process is a process of determining whether oil replacement is necessary. The threshold yth is set to a value of the output variable y3 when oil replacement is necessary.

When the CPU 42 determines that the value of the output variable y3 is equal to or larger than the threshold yth (S24: YES), the CPU 42 determines that oil replacement is necessary (S26). When the process of S26 is completed or when the determination result in the process of S24 is negative, the CPU 42 executes an addressing process for addressing the result obtained through the processes of S22 to S26 (S28).

Figure 10:
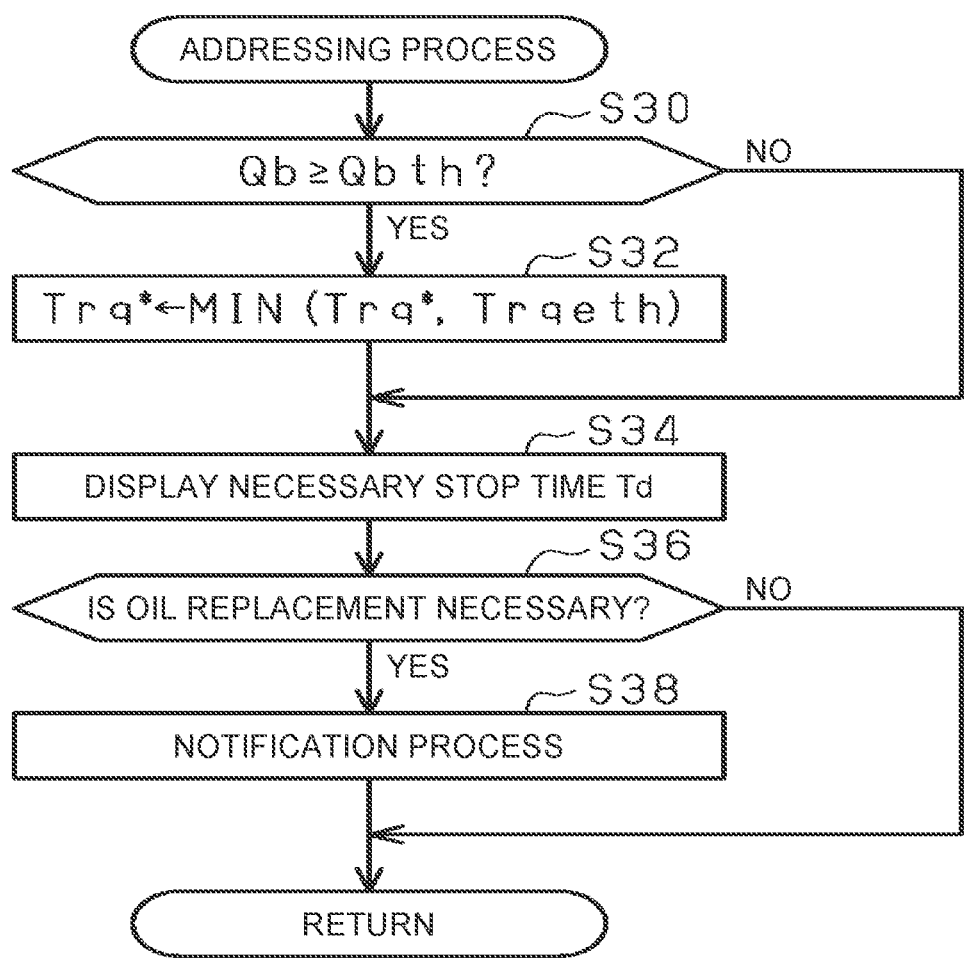
FIG. 10 is a flowchart illustrating details of an addressing process according to the first embodiment.

FIG. 10 illustrates details of the addressing process. In a series of processes illustrated in FIG. 10, the CPU 42 first determines whether the air bubble amount Qb is equal to or larger than a threshold Qbth (S30). The threshold Qbth is set based on a value of the air bubble amount Qb at which the oil cannot exert desired performance when the air bubble amount further increases. When the CPU 42 determines that the air bubble amount Qb is equal to or larger than the threshold Qbth (S30: YES), the CPU 42 substitutes a smaller one of an upper limit guard value Trqeth and the driving torque command value Trq* output through the driving torque setting process M10 into the driving torque command value Trq* to be input to each of the driving force distribution process M12, the gear ratio setting process M14, and the line pressure command value setting process M16 (S32). Therefore, the line pressure command value Pr* is limited to a smaller value. Thus, the CPU 42 operates the hydraulic control circuit 26a to limit, to a smaller value, the pressure of the hydraulic oil output from the hydraulic control circuit 26a.

When the process of S32 is completed or when the determination result in the process of S30 is negative, the CPU 42 operates a display 70 to display visual information of the necessary stop time Td on the display 70 (S34).

The CPU 42 determines whether the process of S26 yields a determination result that oil replacement is necessary (S36). When the CPU 42 determines that the process of S26 yields this determination result (S36: YES), the CPU 42 operates the display 70 to execute a notification process for notifying a user that oil replacement is necessary (S38).

When the process of S38 is completed or when the determination result in the process of S36 is negative, the CPU 42 completes the process of S28 illustrated in FIG. 3. Referring back to FIG. 3, when the process of S28 is completed or when the determination result in the process of S12 is negative, the CPU 42 temporarily terminates the series of processes illustrated in FIG. 3.

Actions and effects of this embodiment are described. The CPU 42 sequentially acquires the accelerator operation amount ACCP, the vehicle speed SPD, and the oil temperature Toil, and calculates the maximum value ACCPmax, the maximum value SPDmax, the average Toilave, the continuous rotation time Tr, and the continuous stop time Ts in each predetermined period. The CPU 42 calculates the values of the output variables y1 to y3 by inputting the values described above to the mapping defined by the mapping data DM, and calculates the air bubble amount Qb based on the values of the output variables y1 to y3. Since the air bubble amount Qb is calculated based on, for example, the maximum value ACCPmax indicating the line pressure as well as the vehicle speed SPD indicating the rotation speed of the rotator in the power transmission apparatus, the air bubble amount Qb can be calculated with high accuracy.

According to this embodiment, the following actions and effects are also attained.

(1) The input variables of the mapping include the average Toilave as a temperature variable indicating a temperature of the oil. Thus, the air bubble amount Qb can be calculated with higher accuracy as compared to a case where the temperature variable is not included.

(2) The maximum value SPDmax and the maximum value ACCPmax representative of the vehicle speed SPD and the accelerator operation amount ACCP in the predetermined period are set as the input variables of the mapping. Thus, information about the rotation status of the rotator and the line pressure can be input to the mapping by using a few variables.

(3) The input variables of the mapping include the continuous rotation time Tr and the continuous stop time Ts. Thus, the air bubble amount Qb can be calculated by reflecting the fact that the air bubble amount decreases during a period in which all the rotators in the power transmission apparatus are stopped, and the air bubble amount increases when any rotator rotates.

(4) The input variables of the mapping include time-series data of continuous rotation times Tr and continuous stop times Ts instead of including a total time of rotation of the rotator of the power transmission apparatus in the predetermined period and a total time of stop of the rotator of the power transmission apparatus in the predetermined period. Thus, when the air bubble amount in the oil differs between, for example, a case where the rotating state and the stopping state of the rotator are frequently repeated in the predetermined period and a case where one rotating state and one stopping state occur, different values having high accuracy can be calculated as the air bubble amount Qb.

(5) The update amount of the air bubble amount Qb is calculated each time as the output variable y1 by using the neural network, and the air bubble amount Qb is updated each time based on the update amount. Thus, the air bubble amount Qb in the oil can be calculated with high accuracy without using values of the input variables in the distant past.

(6) The output variable y2 indicates the necessary stop time Td of the rotator that is necessary to reduce the air bubble amount in the oil to the specified amount or smaller. Thus, the user can be informed of the length of time required to terminate a state in which the amount of air bubbles is excessive.

(7) The output variable y3 is the determination variable indicating whether oil replacement is necessary. Thus, determination that is difficult based only on the air bubble amount in the oil can be achieved by using machine learning.

(8) When the CPU 42 determines that the air bubble amount Qb is equal to or larger than the threshold Qbth, the CPU 42 limits the driving torque command value Trq* to the upper limit guard value Trqeth or smaller. Therefore, the line pressure command value Pr* can be limited to a smaller value. Thus, it is possible to suppress a further increase in the air bubble amount in the oil.

A second embodiment of the present disclosure is described below with reference to the drawings, focusing on a difference from the first embodiment.

In the embodiment described above, the input variables of the mapping include the continuous rotation time Tr and the continuous stop time Ts. For example, when the vehicle speed SPD and the accelerator operation amount ACCP are zero, the rotator in the power transmission apparatus is generally stopped. When the vehicle speed SPD and the accelerator operation amount ACCP are larger than zero, the rotator may be rotating. In view of those facts, in this embodiment, the input variables of the mapping include time-series data of vehicle speeds SPD and accelerator operation amounts ACCP instead of including the continuous rotation time Tr and the continuous stop time Ts.

Figure 11:
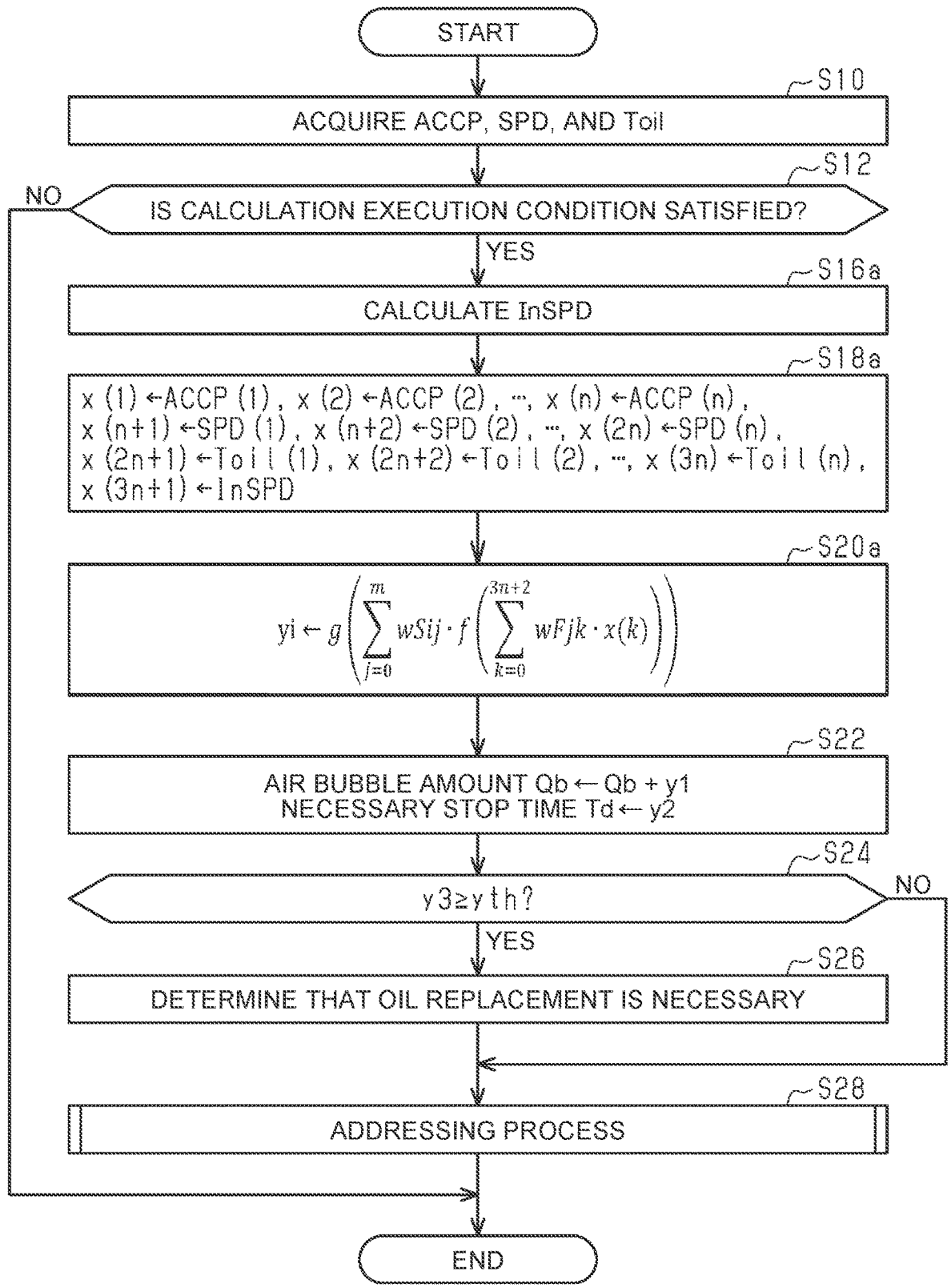
FIG. 11 is a flowchart illustrating a procedure of a process to be executed by a control apparatus according to a second embodiment of the present disclosure.

FIG. 11 illustrates a procedure of a process to be executed by a control apparatus according to this embodiment. The process illustrated in FIG. 11 is implemented such that the CPU 42 repeatedly executes a program stored in the ROM 44 in, for example, every predetermined period. In FIG. 11, processes corresponding to the processes illustrated in FIG. 3 are represented by the same step numbers for convenience, and their description is omitted.

In a series of processes illustrated in FIG. 11, when the determination result in the process of S12 is positive, the CPU 42 calculates the cumulative vehicle speed quantitative value InSPD (S16a). The CPU 42 substitutes accelerator operation amounts ACCP(1), ACCP(2), . . . , vehicle speeds SPD(1), SPD(2), - - - , and oil temperatures Toil(1), Toil(2), - - - in the predetermined period and the cumulative vehicle speed quantitative value InSPD into input variables x(1) to x(3n+1) of the mapping (S18a). In FIG. 11, "n" represents each of the sampling count of the accelerator operation amounts ACCP(1), ACCP(2), - - - , the sampling count of the vehicle speeds SPD(1), SPD(2), - - - , and the sampling count of the oil temperatures Toil(1), Toil(2), - - - . FIG. 11 illustrates an example in which accelerator operation amounts ACCP(1) to ACCP(n) are substituted into input variables x(1) to x(n), vehicle speeds SPD(1) to SPD(n) are substituted into input variables x(n+1) to x(2n), and oil temperatures Toil(1) to Toil(n) are substituted into input variables x(2n+1) to x(3n).

Next, the CPU 42 calculates values of the output variables y1 to y3 by substituting the input variables x(1) to x(3n+1) determined through the process of S18a into mapping defined by the mapping data DM (S20a). The mapping used in this case is similar to the mapping illustrated in FIG. 3 except that the input variables are different.

When the process of S20a is completed, the CPU 42 proceeds to the process of S22. According to this embodiment, the input variables of the mapping include the time-series data of vehicle speeds SPD and accelerator operation amounts ACCP. Thus, even though the input variables do not include the continuous rotation time Tr and the continuous stop time Ts, the values of the output variables y1 to y3 that reflect those pieces of information can be calculated.

A third embodiment of the present disclosure is described below with reference to the drawings, focusing on a difference from the second embodiment.

In the embodiments described above, the fully connected feedforward neural network is used. In this embodiment, a so-called recurrent neural network is used. The recurrent neural network has a recurrent connection structure in which a previous value of a node of an intermediate layer or a previous value of a node of an output layer is reflected when a current value of an output variable is newly calculated. The recurrent neural network is used to output values of the output variables y1 to y3 that reflect previous records of the line pressure and the rotation speed of the rotor of the power transmission apparatus. That is, when current values of the output variables are newly calculated, the previous values of the input variables are reflected through the recurrent connection of the recurrent neural network. Thus, the previous records of the line pressure and the rotation speed of the rotor of the power transmission apparatus can be reflected in the values of the output variables y1 to y3. In particular, long short-term memory (LSTM) is used in this embodiment as an algorithm for satisfactorily performing learning that reflects influence of long-term time-series data in the past in the recurrent neural network. In this embodiment, the output variable y1 among the output variables of LSTM is defined as the air bubble amount Qb.

Figure 12:
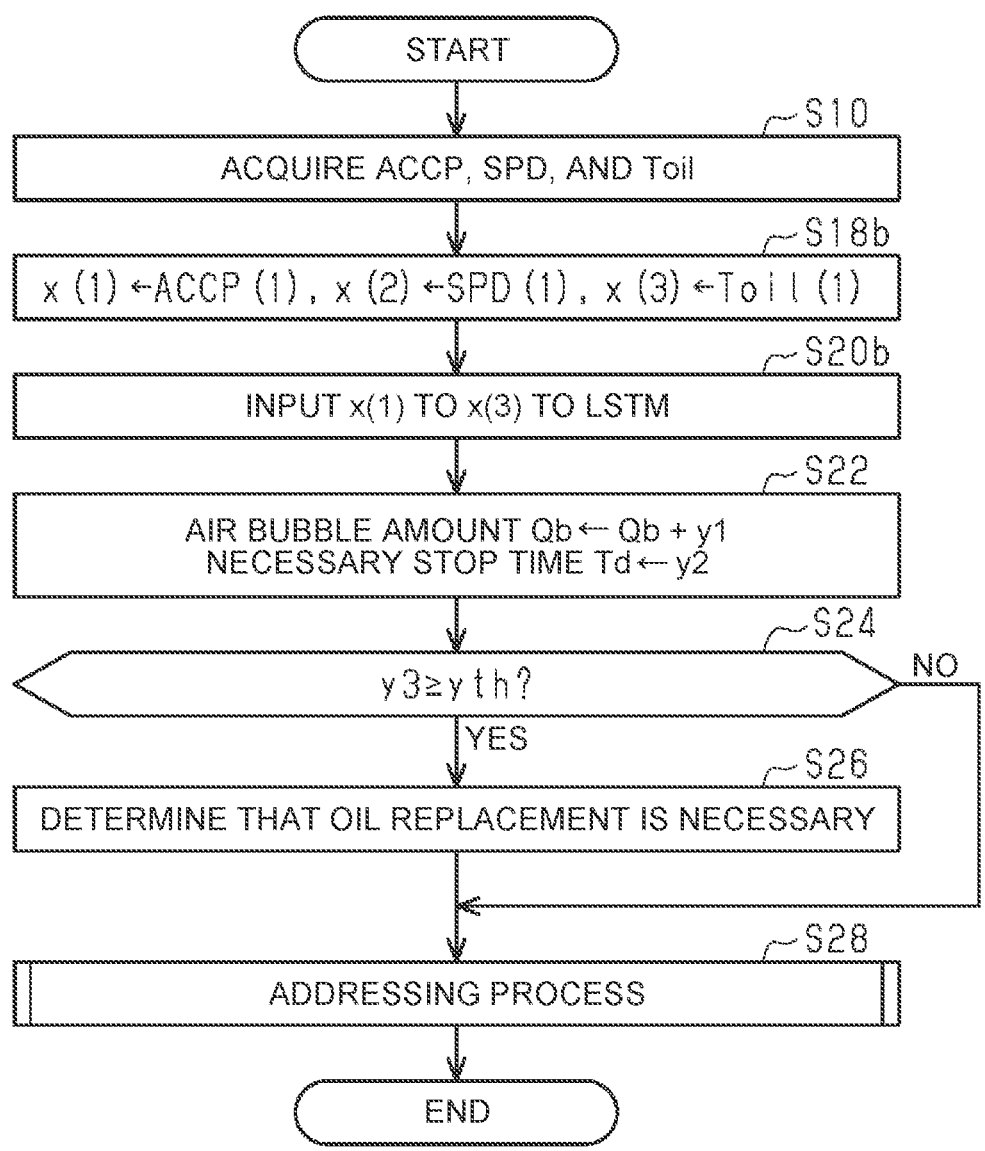
FIG. 12 is a flowchart illustrating a procedure of a process to be executed by a control apparatus according to a third embodiment of the present disclosure.

FIG. 12 illustrates a procedure of a process to be executed by a control apparatus according to this embodiment. The process illustrated in FIG. 12 is implemented such that the CPU 42 repeatedly executes a program stored in the ROM 44 in, for example, every predetermined period. In FIG. 12, processes corresponding to the processes illustrated in FIG. 11 are represented by the same step numbers for convenience, and their description is omitted.

In a series of processes illustrated in FIG. 12, when the process of S10 is completed, the CPU 42 substitutes the accelerator operation amount ACCP, the vehicle speed SPD, and the oil temperature Toil acquired in the process of S10 into input variables x(1) to x(3) of LSTM serving as mapping defined by the mapping data DM (S18b). The CPU 42 calculates values of the output variables y1 to y3 by inputting the input variables x(1) to x(3) to LSTM (S20b). LSTM according to this embodiment is a function approximator configured to output the output variables y1 to y3 based on the input variables x(1) to x(3). When the process of S20b is completed, the CPU 42 proceeds to the process of S22.

In this embodiment, the values of the output variables y1 to y3 are sequentially calculated by inputting the accelerator operation amount ACCP, the vehicle speed SPD, and the oil temperature Toil to LSTM each time. Thus, the air bubble amount Qb is directly calculated and the value of the output variable y3 serving as the determination variable is also calculated based on the records of the line pressure and the rotation speed of the rotor of the power transmission apparatus.

A fourth embodiment of the present disclosure is described below with reference to the drawings, focusing on a difference from the third embodiment.

Figure 13:
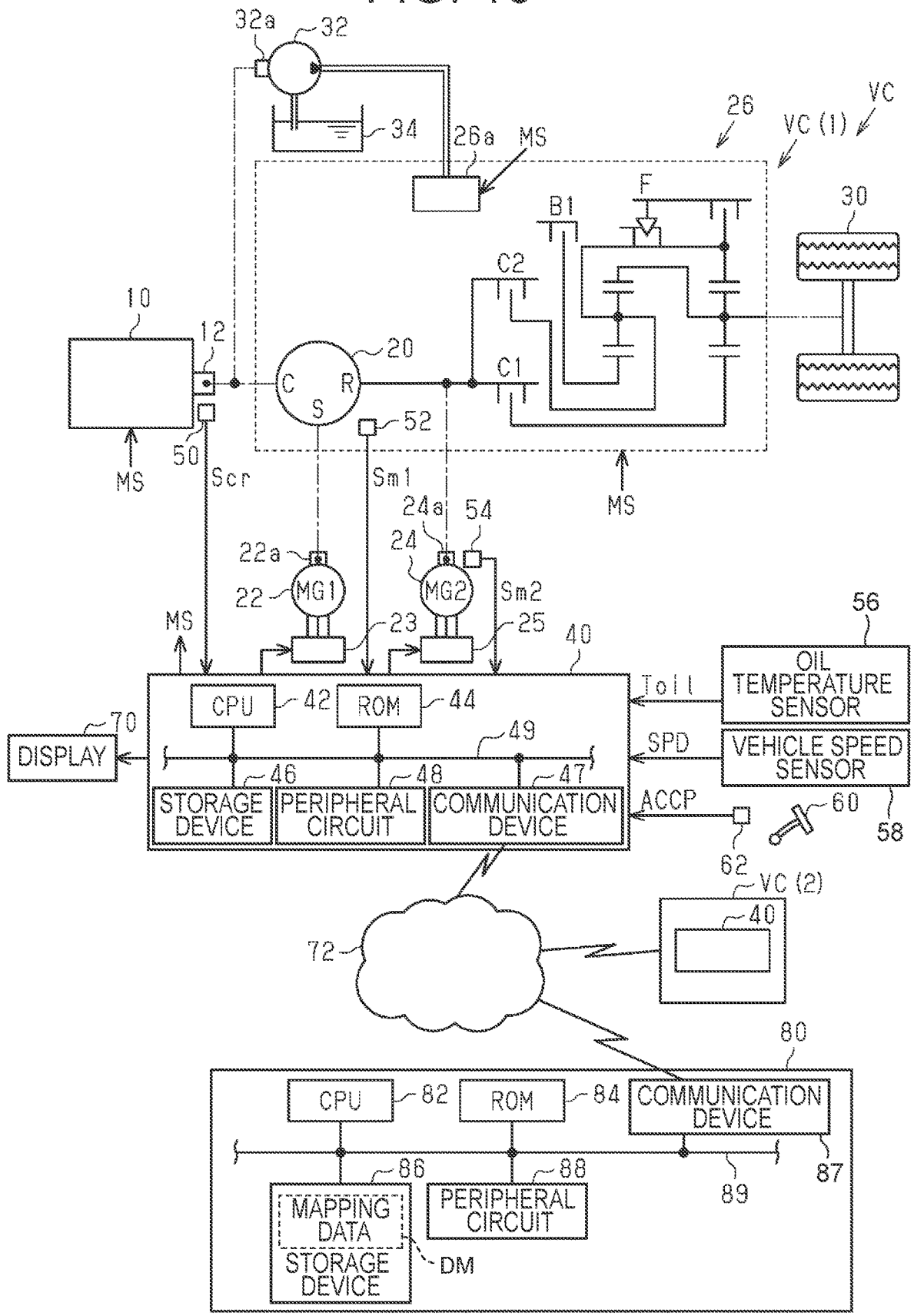
FIG. 13 is a diagram illustrating the configuration of a vehicle control system according to a fourth embodiment of the present disclosure.

In this embodiment, the values of the output variables y1 to y3 are calculated outside the vehicle VC(1). FIG. 13 illustrates the configuration of a system according to this embodiment. Among members illustrated in FIG. 13, members corresponding to the members illustrated in FIG. 1 are represented by the same reference symbols for convenience.

As illustrated in FIG. 13, the control apparatus 40 includes a communication device 47. The communication device 47 communicates with a data analysis center 80 via a network 72 outside the vehicle VC(1).

The data analysis center 80 analyzes data transmitted from a plurality of vehicles VC(1), VC(2), . . . . The data analysis center 80 includes a CPU 82, a ROM 84, a storage device 86, a peripheral circuit 88, and a communication device 87, which are communicable with each other via a local network 89. The storage device 86 is an electrically rewritable non-volatile memory. The storage device 86 stores mapping data DM.

Figure 14B:
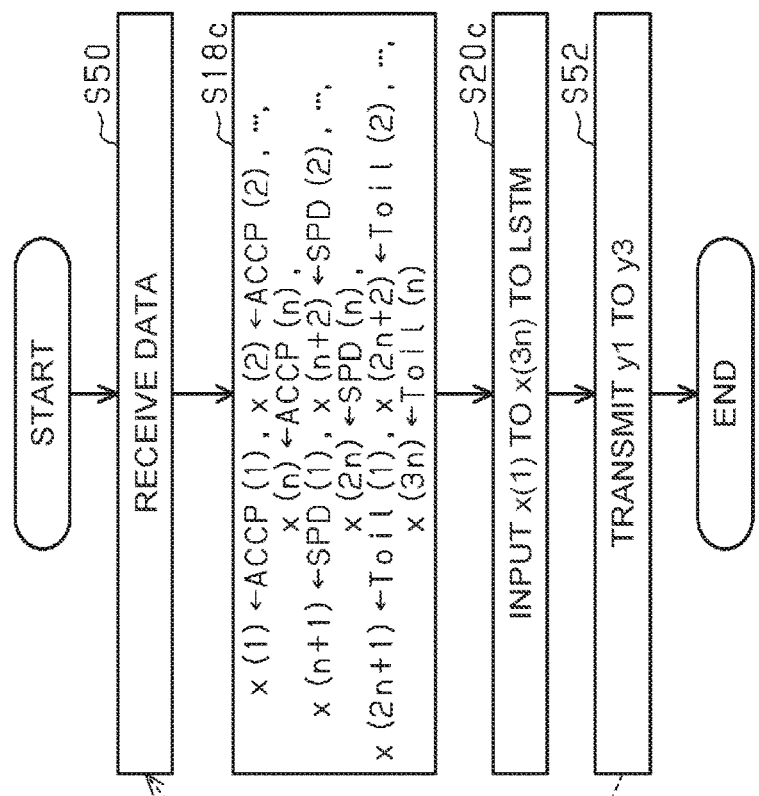
FIG. 14B is a flowchart illustrating a procedure of a process to be executed by the vehicle control system of the fourth embodiment.
Figure 14A:
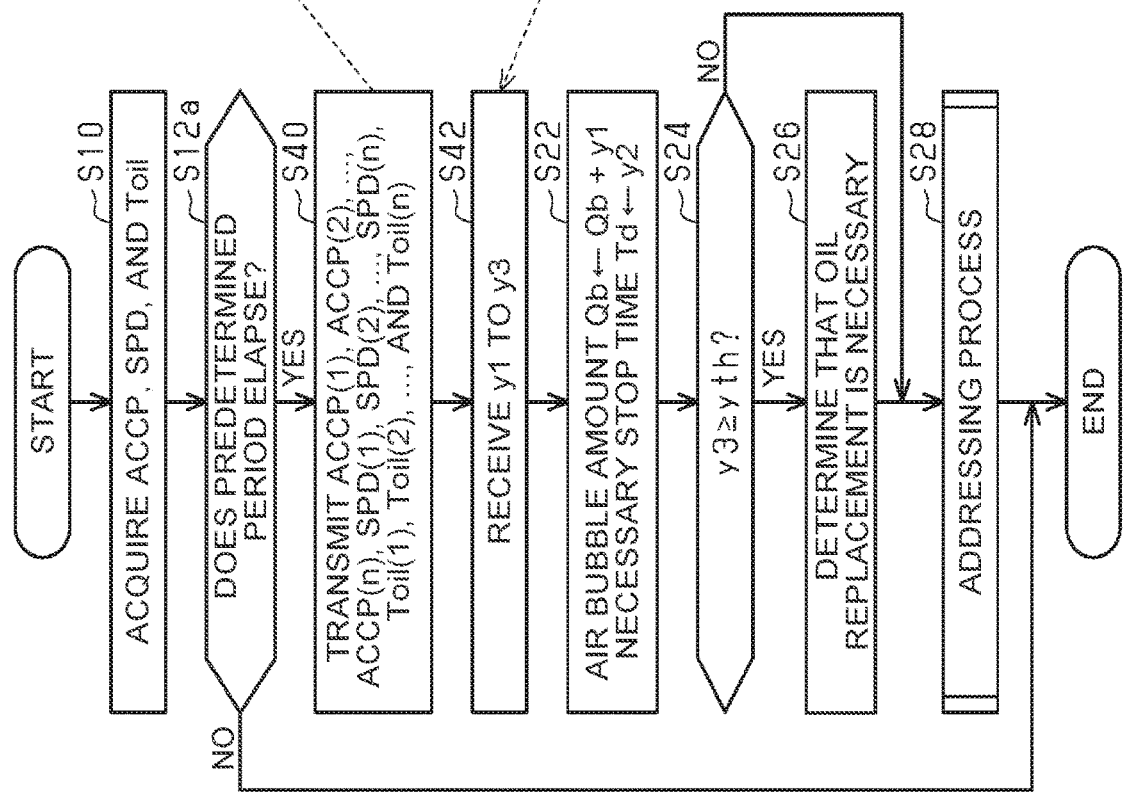
FIG. 14A is a flowchart illustrating a procedure of a process to be executed by the vehicle control system of the fourth embodiment.

FIG. 14A and FIG. 14B illustrate procedures of processes to be executed by the system illustrated in FIG. 13. The process illustrated in FIG. 14A is implemented such that the CPU 42 executes a program stored in the ROM 44 illustrated in FIG. 13. The process illustrated in FIG. 14B is implemented such that the CPU 82 executes a program stored in the ROM 84. The processes illustrated in FIG. 14A and FIG. 14B are described below along the time sequence of processes related to air bubbles.

In a series of processes illustrated in FIG. 14A, when the process of S10 is completed, the CPU 42 determines whether a predetermined period elapses from transmission of data previously acquired through the process of S10 (S12a). When the CPU 42 determines that the predetermined period elapses (S12a: YES), the CPU 42 operates the communication device 47 to transmit time-series data of accelerator operation amounts ACCP, vehicle speeds SPD, and oil temperatures Toil in the predetermined period (S40). FIG. 14A illustrates an example in which "n" pieces of data corresponding to the individual sampling counts equal to each other are transmitted as the time-series data of accelerator operation amounts ACCP, vehicle speeds SPD, and oil temperatures Toil.

As illustrated in FIG. 14B, the CPU 82 receives the data transmitted through the process of S40 (S50). The CPU 82 substitutes the time-series data of accelerator operation amounts ACCP, vehicle speeds SPD, and oil temperatures Toil into the input variables of LSTM serving as mapping defined by the mapping data DM (S18c). This process is equivalent to the process related to the input variables x(1) to x(3n) in the process of S18a in FIG. 11.

The CPU 82 calculates values of the output variables y1 to y3 by inputting the input variables x(1) to x(3n) generated through the process of S18c to LSTM (S20c). That is, LSTM according to this embodiment is a function approximator configured to output the output variables y1 to y3 based on the input variables x(1) to x(3n).

When the process of S20c is completed, the CPU 82 operates the communication device 87 to transmit the values of the output variables y1 to y3 (S52). When the process of S52 is completed, the CPU 82 temporarily terminates the series of processes illustrated in FIG. 14B.

As illustrated in FIG. 14A, the CPU 42 receives the values of the output variables y1 to y3 (S42), and proceeds to the process of S22. According to this embodiment, the calculation load on the CPU 42 can be reduced by executing the calculation process for the values of the output variables y1 to y3 outside the vehicle VC(1). For example, when the user visits a repair shop for oil replacement, correctness of the determination result for the necessity of oil replacement may be evaluated, and the mapping data DM may be updated based on the evaluation. In this case, the number of pieces of training data for relearning can easily be increased by collecting pieces of data from the vehicles VC(1), VC(2), . . . .

The following are correspondences between the matters in the embodiments described above and the matters in the "SUMMARY" section. The correspondences are described below in the order of description in the "SUMMARY" section.

The execution device corresponds to the CPU 42 and the ROM 44 of FIG. 1 and the CPUs 42 and 82 and the ROMs 44 and 84 of FIG. 13. The storage device corresponds to the storage device 46 of FIG. 1 and the storage device 86 of FIG. 13. The mapping data corresponds to the mapping data DM. The speed variable corresponds to the maximum value SPDmax of FIG. 3, the vehicle speed SPD of FIG. 11, FIG. 12, FIG. 14A, and FIG. 14B, and the cumulative vehicle speed quantitative value InSPD of FIG. 3 and FIG. 11. The pressure variable corresponds to the maximum value ACCPmax of FIG. 3 and the accelerator operation amount ACCP of FIG. 11, FIG. 12, FIG. 14A, and FIG. 14B. The air bubble variable corresponds to the output variables y1 and y2. The acquisition process corresponds to the processes of S14 and S16 in FIG. 3, the processes of S10 and S16a in FIG. 11, and the process of S10 in FIG. 12 and FIG. 14A. The calculation process corresponds to the processes of S20, S20a, S20b, and S20c. The temperature variable corresponds to the average Toilave of FIG. 3 and the oil temperature Toil of FIG. 11, FIG. 12, FIG. 14A, and FIG. 14B. The stop time variable corresponds to the continuous stop time Ts. The rotation time variable corresponds to the continuous rotation time Tr. The input variable input to the mapping through the acquisition process and the calculation process corresponds to the processes in FIG. 11, FIG. 14A, and FIG. 14B. The function approximator corresponds to the neural network for use in the processes of S20 and S20a. The recurrent neural network corresponds to LTSM for use in the processes of S20b and S20c. The determination variable corresponds to the output variable y3. The hydraulic control device corresponds to the hydraulic control circuit 26a. The addressing process corresponds to the process of S32. The notification device corresponds to the display 70. The first execution device corresponds to the CPU 42 and the ROM 44. The second execution device corresponds to the CPU 82 and the ROM 84. The external transmission process corresponds to the process of S52. The vehicle-side reception process corresponds to the process of S42.

The embodiments may be modified as follows. The embodiments and the following modified examples may be combined without causing any technical contradiction.

First, the speed variable is described below.

In the process in FIG. 3, the maximum value SPDmax is used as the speed variable, but the speed variable is not limited to the maximum value SPDmax. For example, the vehicle speed SPD may be divided into a plurality of groups in terms of levels, groups to which the vehicle speed SPD belongs may be extracted, and the vehicle speed SPD in a set of variables associated only with the extracted groups may be used as the speed variable. Each variable indicates a time during which the vehicle speed SPD belongs to the group. For example, the speed variable may also be an average of vehicle speeds SPD.

The speed variable is not limited to the vehicle speed SPD or the amount representative of the vehicle speed SPD in the predetermined period that is obtained by processing the vehicle speed SPD based on its level. For example, the speed variable may be a rotation speed of each rotator of the transmission 26, a rotation speed of the crankshaft 12 of the internal combustion engine 10 based on the output signal Scr, a rotation speed of the rotational shaft 22a based on the output signal Sm1, a rotation speed of the rotational shaft 24a based on the output signal Sm2, or an amount representative of each rotation speed in the predetermined period that is obtained by processing the rotation speed based on its level. For example, the speed variable may also be data on a set of a gear ratio of the transmission 26 and the vehicle speed SPD or the amount representative of the vehicle speed SPD in the predetermined period that is obtained by processing the vehicle speed SPD based on its level. By using both the gear ratio and the vehicle speed SPD, the rotation speed of the rotator in the transmission 26 and the rotation speed of each rotator of the power split device 20 can be grasped more accurately as compared to a case where the vehicle speed SPD is used alone. In view of the fact that an approximate vehicle speed SPD can be grasped based on the gear ratio even though both the gear ratio and the vehicle speed SPD are not used, the speed variable may be constituted by the gear ratio alone.

Next, the pressure variable is described.

In the process in FIG. 3, the maximum value ACCPmax of the accelerator operation amount ACCP is used as the pressure variable, but the pressure variable is not limited to the maximum value ACCPmax. For example, the accelerator operation amount ACCP may be divided into a plurality of groups in terms of levels, groups to which the accelerator operation amount ACCP belongs may be extracted, and the accelerator operation amount ACCP in a set of variables associated only with the extracted groups may be used as the pressure variable. Each variable indicates a time during which the accelerator operation amount ACCP belongs to the group. For example, the pressure variable may also be an average of accelerator operation amounts ACCP.

The pressure variable is not limited to the accelerator operation amount ACCP or the amount representative of the accelerator operation amount ACCP in the predetermined period that is obtained by processing the accelerator operation amount ACCP based on its level. For example, the pressure variable may be the driving torque command value Trq* or an amount representative of the driving torque command value Trq* in the predetermined period that is obtained by processing the driving torque command value Trq* based on its level. For example, the pressure variable may also be a variable such as the line pressure command value Pr* related to the hydraulic pressure of the hydraulic oil to be used for driving in the transmission 26, or an amount representative of this variable in the predetermined period that is obtained by processing the value of the variable based on its level.

Next, the temperature variable is described.

In the process in FIG. 3, the average Toilave is used as the temperature variable, but the temperature variable is not limited to the average Toilave. For example, the oil temperature Toil may be divided into a plurality of groups in terms of levels, groups to which the oil temperature Toil belongs may be extracted, and the oil temperature Toil in a set of variables associated only with the extracted groups may be used as the temperature variable. Each variable indicates a time during which the oil temperature Toil belongs to the group.

Next, the stop time variable and the rotation time variable are described.

In the process in FIG. 3, the continuous stop time Ts in the predetermined period before the determination execution condition is satisfied is used as the stop time variable, but the stop time variable is not limited to the continuous stop time Ts. For example, the stop time variable may be a cumulative value of stop times in the period before the determination execution condition is satisfied. When a plurality of continuous stop times Ts in the period before the determination execution condition is satisfied is defined as amounts other than zero, the cumulative value of stop times corresponds to the sum of the continuous stop times Ts, and is a one-dimensional amount. Assuming that the period before the determination execution condition is satisfied is a predetermined length of time, a cumulative value of rotation times in the period before the determination execution condition is satisfied is determined by subtracting the cumulative value of stop times from the period. Thus, the rotation time variable need not be included in the input variables of the mapping though the stop time variable is included.

In the process in FIG. 3, the continuous rotation time Tr in the predetermined period before the determination execution condition is satisfied is used as the rotation time variable, but the rotation time variable is not limited to the continuous rotation time Tr. For example, the rotation time variable may be a cumulative value of rotation times in the period before the determination execution condition is satisfied. When a plurality of continuous rotation times Tr in the period before the determination execution condition is satisfied is defined as amounts other than zero, the cumulative value of rotation times corresponds to the sum of the continuous rotation times Tr, and is a one-dimensional amount. Assuming that the period before the determination execution condition is satisfied is a predetermined length of time, a cumulative value of stop times in the period before the determination execution condition is satisfied is determined by subtracting the cumulative value of rotation times from the period. Thus, the stop time variable need not be included in the input variables of the mapping though the rotation time variable is included.

Next, the time-series data serving as the input variables is described.

In the examples illustrated in FIG. 11, FIG. 14A, and FIG. 14B, the time-series data of accelerator operation amounts ACCP serving as the pressure variable and the time-series data of vehicle speeds SPD serving as the speed variable are set to equal sampling counts and set as the input variables of the neural network, but the sampling counts are not limited to those in this case.

Next, description is given of a neural network in which the output variables include a variable indicating the air bubble amount itself.

The neural network in which the output variables include the variable indicating the air bubble amount itself is not limited to the recurrent neural network. For example, the output variable y1 may be obtained as the air bubble amount itself by including an air bubble amount earlier by one step in the input variables of the fully connected feedforward neural network exemplified in the processes of S20 and S20a.

Next, the input variables of the fully connected feedforward network are described.

The fully connected feedforward network in which the input variables include an air bubble amount earlier by one step is not limited to the network in which the output variables include the air bubble amount itself. In a case where the output variable y2 is included, the value of the output variable y2 can be calculated with higher accuracy by including the air bubble amount earlier by one step in the input variables as compared to a case where the air bubble amount earlier by one step is not included.

The input variables of the recurrent neural network are described.

The input variables of the recurrent neural network are not limited to the input variables including the pressure variable such as the accelerator operation amount ACCP or the time-series data of pressure variables such as the time-series data of accelerator operation amounts ACCP, and the speed variable such as the vehicle speed SPD or the time-series data of speed variables such as the time-series data of vehicle speeds SPD. For example, the pressure variable may include the maximum value ACCPmax of the accelerator operation amount ACCP or an average of accelerator operation amounts ACCP. For example, the accelerator operation amount ACCP may also be divided into a plurality of groups in terms of levels, groups to which the accelerator operation amount ACCP belongs may be extracted, and the accelerator operation amounts ACCP in a set of variables associated only with the extracted groups may be used as the pressure variable. Each variable indicates a time during which the accelerator operation amount ACCP belongs to the group. Further, time-series data of those pressure variables may be set as the input variables. With the speed variable and the pressure variable constituted by using the variables representative of the speed and the pressure in the specified period, the recurrent neural network can be trained by reflecting records in the distant past from the current time despite the size of time steps when influence of time steps before the current time is reflected in the training of the recurrent neural network.

The input variables of the recurrent neural network may include a previous air bubble amount Qb itself. As compared to a case where the input variables do not include the previous air bubble amount Qb itself, it is possible to reduce, in the calculation of the air bubble amount Qb, a time interval between the current time and a timing in the past whose influence needs to be reflected in the values of the output variables.

Next, the output variables of the recurrent neural network are described.

The embodiments described above are directed to the example in which the output variables of the recurrent neural network include the variable indicating the air bubble amount Qb itself. The output variables are not limited to those in this example. For example, the output variables may include an update amount of the air bubble amount Qb.

Next, the recurrent neural network is described.

The recurrent neural network is not limited to LSTM. For example, a gated recurrent unit (GRU) may be employed. The recurrent neural network is not even limited to the gated RNN.

Next, the mapping is described.

The neural network is not limited to the fully connected feedforward network and the recurrent neural network. For example, the time-series data may be input by using a one-dimensional convolutional neural network. The trained model using machine learning is not limited to the neural network.

The mapping is not limited to the mapping configured to output the three output variables, that is, the update amount of the air bubble amount or the air bubble amount itself, the necessary stop time Td, and the determination variable. For example, the update amount of the air bubble amount or the air bubble amount itself and the determination variable may be output as the output variables, but the necessary stop time Td need not be output as the output variable. For example, the update amount of the air bubble amount or the air bubble amount itself may be output as the output variable, but the necessary stop time Td and the determination variable need not be output as the output variables.

The mapping is not limited to the mapping in which the update amount of the air bubble amount or the air bubble amount itself is the output variable serving as the air bubble variable. For example, the mapping may be a discriminative model configured to determine whether the air bubble amount is equal to or larger than a specified amount. The discriminative model may show a result of the determination of whether the air bubble amount is equal to or larger than the specified amount based on a positive or negative sign of the output variable.

In the processes of S20 and S20a, the neural network having one intermediate layer is exemplified, but the neural network is not limited to this neural network. The neural network may have two or more intermediate layers. In the processes of S20 and S20a, the hyperbolic tangents are exemplified as the activation functions f and g, but the activation functions f and g are not limited to the hyperbolic tangents. For example, a part of the activation function g that outputs the output variables y2 and y3 may be a rectified linear unit (ReLU). When the output variable y1 indicates the air bubble amount, the entire activation function g may be the ReLU. For example, the activation function g may also be a logistic sigmoid function when showing, as the output variable, a probability of whether the air bubble amount is equal to or larger than the specified amount in place of the update amount of the air bubble amount and the necessary stop time Td.

Next, the notification device is described.

In the process of S38, the display 70 is the notification device to execute the process of displaying visual information as the notification process, but the notification device is not limited to the display 70. For example, the notification device may be a loudspeaker, and the notification process may be executed by outputting an audio signal through an operation of the loudspeaker.

Next, the addressing process is described.

The process for reducing the pressure of the hydraulic oil is not limited to the process of S32. For example, the line pressure command value Pr* itself may be used for the pressure reducing process. For example, this process may be implemented such that a smaller one of the upper limit guard value and the line pressure command value Pr* output through the line pressure command value setting process M16 is input to the gear shifting operation process M18 to reduce the upper limit guard value. For example, this process may also be implemented such that a value obtained by multiplying the line pressure command value Pr* output through the line pressure command value setting process M16 by a positive coefficient smaller than "1" is input to the gear shifting operation process M18. For example, the pressure reducing process may also be a process of limiting, to a smaller value, the magnitude of the accelerator operation amount ACCP to be input to the driving torque setting process M10.

The addressing process need not essentially include all the processes illustrated in FIG. 10 or processes corresponding to the processes illustrated in FIG. 10.

Next, the oil is described.

The oil is not limited to the oil to be used as the hydraulic oil. For example, the oil may be used only for lubrication. For example, when the driven shaft 32a of the oil pump 32 is coupled to the crankshaft 12 of the internal combustion engine 10 in this case, the pressure of the oil may change because the amount of oil ejected from the oil pump 32 changes depending on the rotation speed of the crankshaft 12. Therefore, it is effective to reduce the pressure through the addressing process when the air bubble amount Qb is equal to or larger than the threshold Qbth.

Next, the vehicle control system is described.

In the processes in FIG. 14A and FIG. 14B, the variables serving as inputs to the neural network are transmitted from the vehicle VC to the data analysis center 80, but the processes are not limited to those in this case. For example, when the process using the neural network is the process of S20, time-series data of vehicle speeds SPD, accelerator operation amounts ACCP, and oil temperatures Toil may periodically be transmitted from the vehicle VC to the data analysis center 80. In this case, the maximum value ACCPmax, the maximum value SPDmax, the average Toilave, and the cumulative vehicle speed quantitative value InSPD are calculated at the data analysis center 80.

The vehicle control system is not limited to the system including the vehicle and the data analysis center 80. For example, the process in FIG. 14B may be executed by a mobile terminal of the user of the vehicle. Further, the vehicle control system is not limited to the system including the vehicle and the mobile terminal of the user of the vehicle. For example, the system may include the vehicle, the mobile terminal of the user of the vehicle, and the data analysis center. For example, this system may be implemented such that the processes of S42, S22 to S28 in FIG. 14A are executed by the mobile terminal, the addressing process of S28 being shown in the processes of S34 to S38 in FIG. 10.

Next, the execution device is described.

The execution device is not limited to the device that includes the CPU 42 (82) and the ROM 44 (84) and executes the software process. For example, the execution device may include a dedicated hardware circuit such as an application-specific integrated circuit (ASIC) configured to execute a hardware process in place of at least a part of the software process in the embodiments. That is, the execution device may have one of the following structures (a) to (c). (a) The execution device includes a processing device configured to execute all the processes described above based on programs, and a program storage device such as a ROM that stores the programs. (b) The execution device includes a processing device configured to execute a part of the processes described above based on programs, a program storage device, and a dedicated hardware circuit configured to execute the remaining processes. (c) The execution device includes a dedicated hardware circuit configured to execute all the processes described above. A plurality of devices or circuits may be provided as the software execution device including the processing device and the program storage device or as the dedicated hardware circuit.

Next, the vehicle is described.

The vehicle is not limited to the vehicle including the transmission 26. Even in a case where the transmission 26 is not provided, the use of the mapping is effective to, for example, make determination about an air bubble amount in lubricating oil for the power split device 20 or an air bubble amount in lubricating oil for the internal combustion engine 10.

The vehicle is not limited to a series-parallel hybrid vehicle. For example, the vehicle may be a series hybrid vehicle or a parallel hybrid vehicle. The vehicle is not limited to the vehicle including the internal combustion engine and the motor generator as the on-board rotating machines. For example, the vehicle may have the internal combustion engine but need not have the motor generator. For example, the vehicle may have the motor generator but need not have the internal combustion engine.

In the embodiments described above, the gear ratio command value Vsft* is set by inputting the driving torque command value Trq* and the vehicle speed SPD, but is not limited to the gear ratio command value Vsft* in this case. For example, the gear ratio command value Vsft* may be set by inputting the accelerator operation amount ACCP and the vehicle speed SPD.

What is claimed is:

1. A vehicle control apparatus comprising an oil condition estimation apparatus to be applied to a vehicle in which oil is agitated by a rotator, the oil condition estimation apparatus comprising:
 a storage device configured to store mapping data for defining mapping, the mapping including, as input variables, a speed variable indicating a rotation speed of the rotator, and a pressure variable indicating a pressure of the oil, and including, as an output variable, an air bubble variable related to air bubbles contained in the oil; and
 a processor programmed
 acquire values of the input variables, and
 calculate a value of the output variable by inputting, to the mapping, the values of the acquired input variables;
 wherein the oil is hydraulic oil whose pressure is adjusted by a hydraulic control device;
 wherein the air bubble variable includes at least one of an air bubble amount in the oil and an update amount of an air bubble amount in the oil; and
 wherein the processor is further programmed to, when the calculated value of the air bubble variable indicates that the air bubble amount is equal to or larger than a threshold, reduce the pressure of the oil by operating the hydraulic control device.

2. The vehicle control apparatus according to claim 1, wherein the input variables further include a temperature variable indicating a temperature of the oil.

3. The vehicle control apparatus according to claim 1, wherein:
 the oil is used to hydraulically drive a transmission to change a gear ratio of the transmission, the transmission being configured to change the gear ratio, which is a ratio between a rotation speed of a rotational shaft of an on-board prime mover and a rotation speed of a driving wheel;
 the speed variable includes a vehicle speed; and
 the pressure variable includes an accelerator operation amount.

4. The vehicle control apparatus according to claim 1, wherein the input variables further include at least one of:
 a stop time variable indicating a time during which the rotator is stopped; and
 a rotation time variable indicating a time during which the rotator is rotating.

5. The vehicle control apparatus according to claim 1, wherein:
 the input variables of the mapping include time-series data of the speed variable and time-series data of the pressure variable;
 the acquiring of the values of the input variables includes acquiring the time-series data of the speed variable and the time-series data of the pressure variable; and
 the calculating of the value of the output variable includes inputting, to the mapping, the acquired time-series data of the speed variable and the acquired time-series data of the pressure variable.

6. The vehicle control apparatus according to claim 1, wherein:
 the air bubble variable includes the update amount of the air bubble amount in the oil;
 the mapping includes a function approximator configured to output the update amount of the air bubble amount by inputting the values of the input variables; and
 the calculating includes repeatedly calculating the value of the output variable by inputting, to the mapping, the values of the input variables that are repeatedly acquired, and updating the air bubble amount based on the value of the output variable that is calculated each time.

7. The vehicle control apparatus according to claim 1, wherein:
 the air bubble variable includes the air bubble amount in the oil; and
 the mapping includes a recurrent neural network configured to output the air bubble amount by inputting the values of the input variables.

8. The vehicle control apparatus according to claim 1, wherein the air bubble variable includes a necessary stop time of the rotator that is necessary to reduce the air bubble amount in the oil to a specified amount or smaller.

9. The vehicle control apparatus according to claim 1, wherein the output variable further includes a determination variable indicating whether replacement of the oil is necessary.

10. The vehicle control apparatus according to claim 9, wherein the processor is further programmed to, when a value of the calculated determination variable is a value indicating that the replacement of the oil is necessary, notify, by operating a notification device, a user that the replacement of the oil is necessary.

11. A vehicle control system comprising the vehicle control apparatus according to claim 10:
 wherein the processor includes a first processor that is provided in the vehicle and a second processor that is not provided in the vehicle;
 wherein the second processor is programmed at least to calculate the value of the determination variable and transmit the calculated value of the determination variable to the first processor; and
 wherein the first processor is programmed at least to receive the calculated value of the determination variable from the second processor notify, by operating the notification device, a user that the replacement of the oil is necessary.

12. A vehicle control system comprising the vehicle control apparatus according to claim 1:
 wherein the processor includes a first processor that is provided in the vehicle and a second processor that is not provided in the vehicle;
 wherein the second processor is programmed at least to calculate the value of the air bubble variable at least the calculation process and transmit the calculated value of the air bubble variable to the first processor; and
 wherein the first processor is programmed at least to receive the calculated value of the air bubble variable from the second processor and reduce the pressure of the oil by operating the hydraulic control device.

13. A vehicle control apparatus comprising an oil condition estimation apparatus to be applied to a vehicle in which oil is agitated by a rotator, the oil condition estimation apparatus comprising:
- a storage device configured to store mapping data for defining mapping, the mapping including, as input variables, a speed variable indicating a rotation speed of the rotator, and a pressure variable indicating a pressure of the oil, and including, as an output variable, an air bubble variable related to air bubbles contained in the oil; and
- a processor programmed to
  - acquire values of the input variables, and
  - calculate a value of the output variable by inputting, to the mapping, the acquired values of the input variables;

wherein the oil hydraulically drives a transmission to change a gear ratio of the transmission, the gear ratio being a ratio between a rotation speed of a rotational shaft of an on-board prime mover and a rotation speed of a driving wheel;

wherein the air bubble variable includes at least one of an air bubble amount in the oil and an update amount of an air bubble amount in the oil; and wherein the processor is further programmed, when the calculated value of the air bubble variable indicates that the air bubble amount is equal to or larger than a threshold, limit a torque of the on-board prime mover to a smaller value.

14. A vehicle control system comprising the vehicle control apparatus according to claim 13:
- wherein the processor includes a first processor that is provided in the vehicle and a second processor that is not provided in the vehicle;
- wherein the second processor is programmed at least to calculate the value of the air bubble variable and transmit the calculated value of the air bubble variable to the first processor; and
- wherein the first processor is programmed at least to receive the calculated value of the air bubble variable from the second processor and limit the torque of the on-board prime mover to a smaller value.

* * * * *